(12) United States Patent
Wu et al.

(10) Patent No.: US 12,171,824 B2
(45) Date of Patent: Dec. 24, 2024

(54) IMMUNE COMPOSITION COMPRISING ANTIGEN AND GLYCOENGINEERED ANTIBODY THEREOF

(71) Applicant: CHO PHARMA INC., Taipei (TW)

(72) Inventors: Chung-Yi Wu, New Taipei (TW); Chien-Yu Chen, Taipei (TW); Ju-Mei Li, Taipei (TW); Kuo-Ching Chu, Taipei (TW)

(73) Assignee: CHO PHARMA, INC., Taipei (TW)

( * ) Notice: Subject to any disclaimer, the term of this patent is extended or adjusted under 35 U.S.C. 154(b) by 302 days.

(21) Appl. No.: 17/453,826

(22) Filed: Nov. 5, 2021

(65) Prior Publication Data

US 2022/0143172 A1 May 12, 2022

Related U.S. Application Data

(60) Provisional application No. 63/178,177, filed on Apr. 22, 2021, provisional application No. 63/110,845, filed on Nov. 6, 2020.

(51) Int. Cl.
*A61K 39/12* (2006.01)
*A61K 39/145* (2006.01)
*A61K 39/21* (2006.01)
*A61K 39/215* (2006.01)
*A61K 39/39* (2006.01)
*C07K 16/10* (2006.01)

(52) U.S. Cl.
CPC ............ *A61K 39/12* (2013.01); *A61K 39/145* (2013.01); *A61K 39/21* (2013.01); *A61K 39/215* (2013.01); *A61K 39/39* (2013.01); *C07K 16/1003* (2023.08)

(58) Field of Classification Search
None
See application file for complete search history.

(56) References Cited

U.S. PATENT DOCUMENTS

| 8,106,170 B2 | 1/2012 | Ter Meulen et al. |
| 10,787,501 B1 | 9/2020 | Babb et al. |
| 2015/0344544 A1 | 12/2015 | Wong et al. |
| 2016/0208009 A1 | 7/2016 | Umana et al. |
| 2019/0256579 A1 | 8/2019 | Graham et al. |

FOREIGN PATENT DOCUMENTS

| EP | 3042952 A1 | 7/2016 | |
| TW | 201613970 A | 4/2016 | |
| WO | WO-2005012360 A2 * | 2/2005 | .......... A61K 39/215 |
| WO | 2015143091 A1 | 9/2015 | |
| WO | 2016123593 A1 | 8/2016 | |
| WO | 2016154118 A1 | 9/2016 | |
| WO | 2020182984 A2 | 9/2020 | |

OTHER PUBLICATIONS

Tala T. Wang, et al.: Anti-HA glycoforms drive B cell affinity selection and determine influenza vaccine efficacy: Cell. Jul. 2, 2015; 162(1): 160-169. doi:10.1016/j.cell.2015.06.026.
Jad Maamarya, et al.: Increasing the breadth and potency of response to the seasonal influenza virus vaccine by immune complex immunization: 10172-10177 | PNAS | Sep. 19. 2017 | vol. 114 | No. 38.
Giuseppe Lofano, et al.: Sci. Immunol. 3, eaat7796 (2018) Aug. 17, 2018 Science Immunology | Research Article 1.
Jun Lan, et al.: Structure of the SARS-COV-2 spike receptor-binding domain bound to the ACE2 receptor: Nature | vol. 581 | May 14, 2020.
Meng Yuan, et al.: Supplementary Materials for "A highly conserved cryptic epitope in the receptor-binding domains of SARS-CoV-2 and SARS-CoV": Published Apr. 3, 2020 on Science First Release DOI: 10.1126/science.abb7269.
Office Action with Search Report dated Feb. 23, 2023.
International Search Report and Written Opinion issued in the corresponding PCT Application No. PCT/US2021/072272 mailed Mar. 2, 2022 (Mar. 2, 2022).

* cited by examiner

*Primary Examiner* — Nicole Kinsey White
(74) *Attorney, Agent, or Firm* — LADAS & PARRY LLP

(57) ABSTRACT

The present disclosure relates to a composition for inducing immune response comprising a glycoengineered antibody or antigen-binding fragment thereof that is specific for an antigen portion having a receptor binding domain (RBD) of a surface protein of a virus. The present disclosure also relates to an immune combination and a method for treating an infection by a virus.

27 Claims, 26 Drawing Sheets
Specification includes a Sequence Listing.

US 12,171,824 B2

IMMUNE COMPOSITION COMPRISING ANTIGEN AND GLYCOENGINEERED ANTIBODY THEREOF

PRIORITY

This application claims the benefit of priority to U.S. Provisional Application No. 63/110,845, filed 6 Nov. 2020 and No. 63/178,177 filed 22 Apr. 2021, which are incorporated herein by reference in its entirety.

SEQUENCE LISTING

This instant application contains a Sequence Listing which has been submitted electronically in ASCII format and is hereby incorporated by reference in its entirety. Said ASCII copy, created on Nov. 5, 2021, is named G4590-10600US_SeqList.txt and is 5 kilobytes in size.

FIELD OF THE DISCLOSURE

The present disclosure relates to an immune composition, particularly, to a composition for inducing immune response comprising glycoengineered antibody thereof.

BACKGROUND OF THE DISCLOSURE

It is well established that host immune defenses come into play at various stages of human disease. During viral infection, for example, antibodies stimulated in response to previous immunization may neutralize incoming viruses prior to attachment and penetration of susceptible target cells. In the event that cells become infected and display virus-associated antigens on their surfaces, cellular immune responses may also be activated. In this latter case, cytotoxic T cells can kill infected cells, thereby limiting progression of the infection. These humoral and cellular immune responses are commonly mounted against infection by a wide variety of viruses, including viruses having DNA or RNA genomes and outer coats composed of protein capsids or membrane envelopes.

Strategies for treating infectious disease often focus on ways to enhance immunity. For instance, the most common method for treating viral infection involves prophylactic vaccines that induce immune-based memory responses. Another method for treating viral infection includes passive immunization via immunoglobulin therapy.

There is still a need for a novel approach to treatment of viral infection.

SUMMARY OF THE DISCLOSURE

The present disclosure relates to a composition for inducing immune response and immune combination for treatment of viral infection.

In one aspect, the present disclosure provides a composition for inducing immune response comprising:

a glycoengineered antibody or antigen-binding fragment thereof that is specific for an antigen portion having a receptor binding domain (RBD) of a surface protein of a virus, wherein the glycoengineered antibody or antigen-binding fragment thereof has a fragment crystallizable region (Fc region) and N-glycan on the Fc region, and the N-glycan is represented by the general formula (I)

wherein:

$$\begin{array}{l}\text{X-Man}\\\qquad\diagdown\\\qquad\quad\text{Man-GlcNAc-GlcNAc-}\\\qquad\diagup\qquad\qquad\qquad |\\\text{Y-Man}\qquad\qquad\quad(\text{Fuc})_{0\,or\,1}\end{array}$$

formula (I)

each of X and Y presents a glycan, and X and Y are identical.

In some embodiments of the disclosure, the composition further comprises the antigen portion having the RBD of the surface protein of the virus. In some embodiments of the disclosure, the antigen portion and the glycoengineered antibody or antigen-binding fragment thereof form an immune complex.

In some embodiments of the disclosure, the surface protein is a spike protein.

Examples of the virus include but are not limited to coronavirus (CoV), human immunodeficiency virus, or Orthomyxoviridae. Examples of the CoV include but are not limited to alpha-CoV, beta-CoV, gamma-CoV, or delta-CoV.

In some embodiments of the disclosure, the antigen portion comprises the amino acid sequence of SEQ ID NO: 1 (RVQPTESIVRFPNITNLCPFGEVFNATR-FASVYAWNRKRISNCVADYSVLYNSASFSTFKC YGVSPTKLNDLCFTNVYADSFVIR-GDEVRQIAPGQTGKIADYNYKLPDDFTGCVIAWNS NNLDSKVGGNYNYLYRLFRKSNLKPFERDIS-TEIYQAGSTPCNGVEGFNCYFPLQSYGFQ PTNGVGYQPYRVVVLSFELLHAPATVCGPKK-STNLVKNKCVNF).

In some embodiments of the disclosure, in formula (I), each of X and Y represents GlcNAc-, GalGlcNAc-, Sia(α2-3)GalGlcNAc-, or Sia(α2-6)GalGlcNAc-.

In some embodiments of the disclosure, the N-glycan is selected from the group consisting of GlcNAc$_2$Man$_3$GlcNAc$_2$(Fuc) (G0F), GlcNAc$_2$Man$_3$GlcNAc$_2$ (G0), Gal$_2$GlcNAc$_2$Man$_3$GlcNAc$_2$ (Fuc) (G2F), Gal$_2$GlcNAc$_2$Man$_3$GlcNAc$_2$ (G2), Sia$_2$(α2-3)Gal$_2$GlcNAc$_2$Man$_3$GlcNAc$_2$(Fuc) (G2S2F (alpha 2,3 linkage)), Sia$_2$(α2-6)Gal$_2$GlcNAc$_2$Man$_3$GlcNAc$_2$(Fuc) (G2S2F (alpha 2,6 linkage)), Sia$_2$(α2-6)Gal$_2$GlcNAc$_2$Man$_3$GlcNAc$_2$ (G2S2 (alpha 2,6 linkage)), and Sia$_2$(α2-3)Gal$_2$GlcNAc$_2$Man$_3$GlcNAc$_2$ (G2S2 (alpha 2,3 linkage)).

In some embodiments of the disclosure, a plurality of the glycoengineered antibodies or antigen-binding fragments thereof are provided in a population, and more than about 90% of the population has the same N-glycan.

In some embodiments of the disclosure, the glycoengineered antibody or antigen-binding fragment thereof comprises a heavy chain variable region comprising the amino acid sequence of SEQ ID NO: 2 (QMQLVQSGTE-VKKPGESLKISCKGSGYGFITYWIGWVRQMPGK-GLEWMGIIYPGDSET RYSPSFQGQVTISADKSINTAY-LQWSSLKASDTAIYYCAGGSGISTPMDVWGQGTTVTV) or a substantially similar sequence thereof, and a light chain variable region comprising the amino acid sequence of SEQ ID NO: 3 (DIQLTQSPDSLAVSLGERATINCKSSQSVL-YSSINKNYLAWYQQKPGQPPKLLIYWASTR ESGVPDRFSGSGSGTDFTLTISSLQAEDVA-VYYCQQYYSTPYTFGQGTKVEIK) or a substantially similar sequence thereof.

The present disclosure also provides an immune combination comprising an effective amount of the composition comprising the glycoengineered antibody or antigen-binding fragment thereof as disclosed herein and an effective amount of the antigen portion having the RBD of the surface protein of the virus and pharmaceutically acceptable carrier and/or adjuvant.

In some embodiments of the disclosure, the immune combination further comprises a vaccine of the virus. In some embodiments of the disclosure, the vaccine comprises the antigen portion.

The present disclosure provides a method for treating an infection by a virus in a subject in need of such treatment comprising administering the composition comprising the glycoengineered antibody or antigen-binding fragment thereof or immune combination as disclosed herein to the subject.

In some embodiments of the disclosure, the composition and the antigen portion are co-administered simultaneously, separately or sequentially or co-administered in combination as a coformulation.

In some embodiments of the disclosure, the immune combination further comprises a vaccine of the virus, and the vaccine is administered prior to the composition.

In some embodiments of the disclosure, the method comprises administering the composition once only.

In some embodiments of the disclosure, the method comprises administering the composition at least two times.

In some embodiments of the disclosure, the method is for priming and subsequently boosting an immune response at different times.

In some embodiments of the disclosure, the method is for neutralizing the virus and/or enhancing antibody-dependent cell-mediated cytotoxicity (ADCC) in the subject.

The present disclosure is described in detail in the following sections. Other characteristics, purposes and advantages of the present disclosure can be found in the detailed description and claims.

BRIEF DESCRIPTION OF THE DRAWINGS

FIG. 16A: Body weight. FIG. 16B: Body temperature. FIG. 16C: Virus RNA copies in lung tissues.

DETAILED DESCRIPTION OF THE DISCLOSURE

Figure 1:
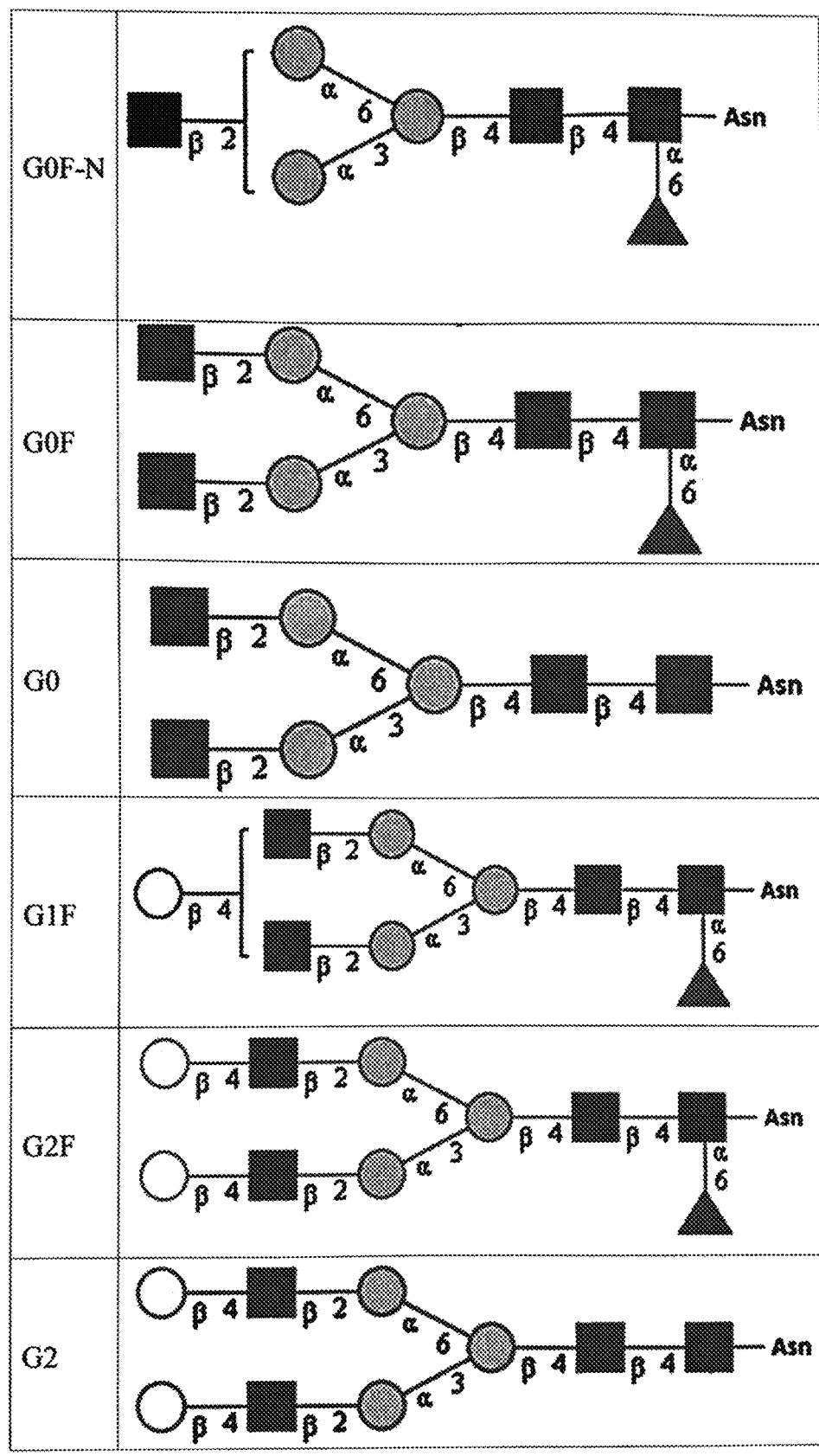
FIG. 1 shows schematic structures of the N-glycans.
Figure 1:
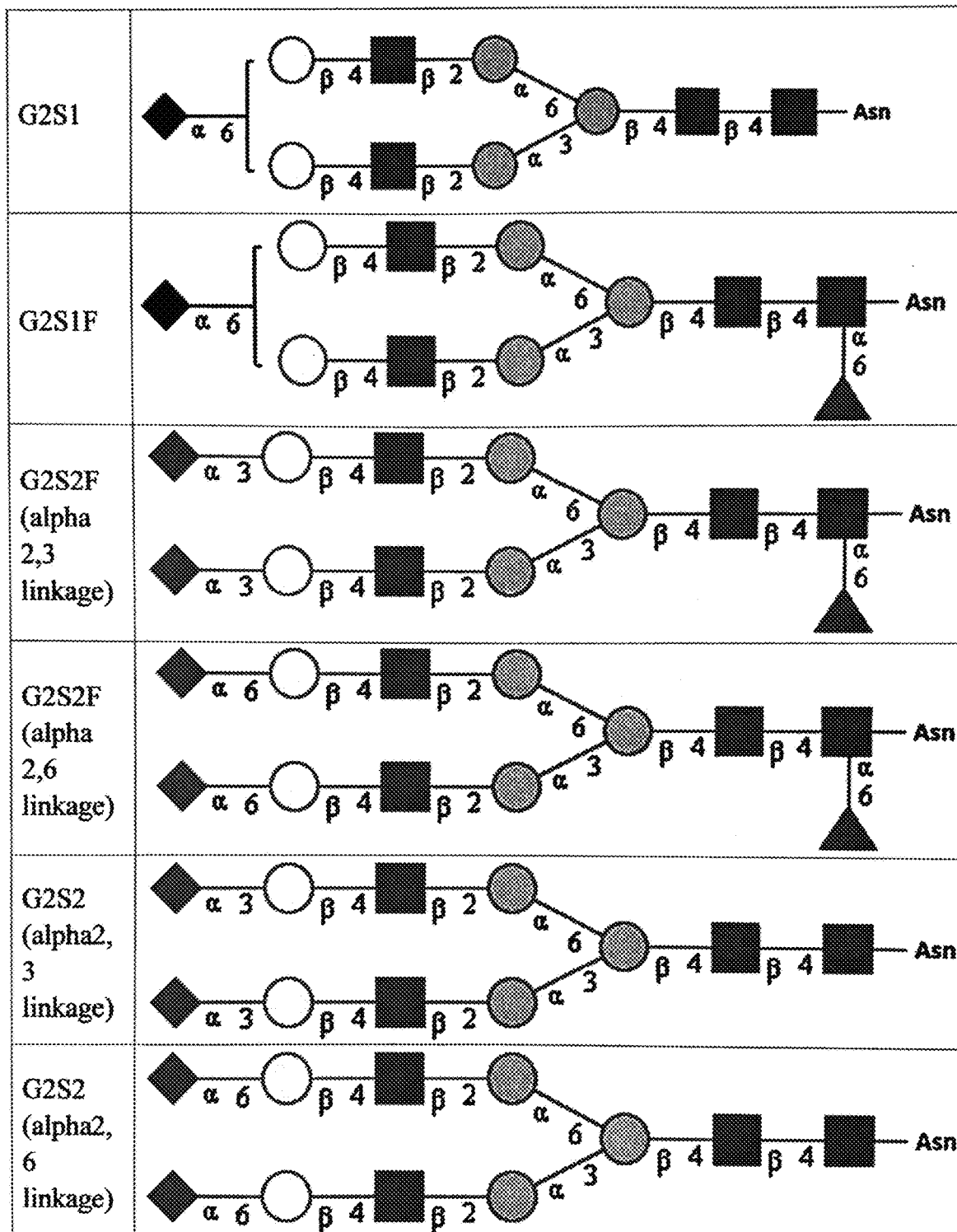

In the description that follows, a number of terms are used and the following definitions are provided to facilitate understanding of the claimed subject matter. Terms that are not expressly defined herein are used in accordance with their plain and ordinary meanings.

Unless otherwise specified, "a" or "an" means "one or more."

The term "and/or" is used to refer to both things or either one of the two mentioned.

As used herein, "immune complex," refers to a structure which forms when at least one target molecule and at least one heterologous Fc region-containing polypeptide bind to one another forming a larger molecular weight complex. Examples of immune complexes are antigen-antibody complexes which can be either soluble or particulate (e.g., an antigen/antibody complex on a cell surface) bind to activating FcTRs, thereby triggering the immune response.

As used herein, the terms "Ag" or "antigen" refer to a substance capable of either binding to an antigen binding region of an immunoglobulin molecule or of eliciting an immune response. As used herein, "antigen" includes, but is not limited to, antigenic determinants, haptens, and immunogens which may be peptides, small molecules, carbohydrates, lipids, nucleic acids or combinations thereof. When used in the context of a B cell mediated immune response in the form of an antibody that is specific for an "antigen", the portion of the antigen that binds to the complementarity determining regions of the variable domains of the antibody (light and heavy) the bound portion may be a linear or three-dimensional epitope.

As used herein, the term "receptor" means any polypeptide expressed by a cell that a virus can bind. Generally, such receptors are naturally present on the surface of a cell, but can be engineered. Receptor polypeptides may be non-covalently or covalently associated with other molecular entities, such as carbohydrates, fatty acids, lipids and the like.

A "binding domain", as used herein, refers to one or more proteins, polypeptides, oligopeptides, or peptides that possesses the ability to specifically recognize and bind to a target (e.g., receptor). A binding domain includes any naturally occurring, synthetic, semi-synthetic, or recombinantly produced binding partner for a biological molecule or another target of interest.

As used herein, the term "surface protein" refers to all surface accessible proteins, e.g., inner and outer membrane proteins, proteins adhering to the cell wall, and secreted proteins.

The term "antibody", as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_{H1}$, $C_{H2}$ and $C_{H3}$. Each light chain comprises a light chain variable region (abbreviated herein as LCVR or $V_L$) and a light chain constant region. The light chain constant region comprises one domain ($C_{L1}$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the disclosure, the FRs of the anti-α-toxin antibody (or antigen-binding portion thereof) may be identical to the human germline sequences or may be naturally or artificially modified. An amino acid consensus sequence may be defined based on a side-by-side analysis of two or more CDRs.

As used herein, the term "complementarity determining region" (CDR) refers to the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared to each other.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex.

As used herein, the term "specifically binding" means that an antibody does not cross-react to any significant extent with other epitopes.

The present disclosure provides a composition for inducing immune response comprising:

a glycoengineered antibody or antigen-binding fragment thereof that is specific for an antigen portion having a receptor binding domain (RBD) of a surface protein of a virus, wherein the glycoengineered antibody or antigen-binding fragment thereof has a fragment crystallizable region (Fc region) and N-glycan on the Fc region, and the N-glycan is represented by the general formula (I)

$$\begin{matrix} X\text{-Man} \\ \phantom{X\text{-}}\diagdown \\ \phantom{XXXX}\text{Man-GlcNAc-GlcNAc-} \\ \phantom{X\text{-}}\diagup \phantom{XXXXXX} | \\ Y\text{-Man} \phantom{XXXX} (\text{Fuc})_{0 \text{ or } 1} \end{matrix} \quad \text{formula (I)}$$

wherein:
each of X and Y presents a glycan, and X and Y are identical.

The receptor-binding domain is a key part of a virus located on its surface protein such as a spike protein that allows it to dock to body receptors to gain entry into cells and lead to infection. The receptor-binding domain is a short immunogenic fragment from a virus that binds to a specific endogenous receptor sequence to gain entry into host cells. Examples of the surface protein include but are not limited to hemagglutinin of influenza, gp120 composed of subunits gp120 and gp41 of human immunodeficiency virus, or spike (S) protein of coronavirus.

In a specific embodiment of the disclosure, the antigen portion comprises a SARS-CoV-2 Spike Protein RBD having the amino acid sequence of SEQ ID NO: 1.

Examples of the virus include but are not limited to, "African Swine Fever Viruses," Arbovirus, Adenoviridae, Arenaviridae, Arterivirus, Astroviridae, Baculoviridae, Bimaviridae, Birnaviridae, Bunyaviridae, Caliciviridae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), Herpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthomyxoviridae (e.g., Influenza A, Influenza B, and parainfluenza), Papiloma virus, Papovaviridae, Paramyxoviridae, Prions, Parvoviridae, Phycodnaviridae, Picomaviridae (e.g. Rhinovirus, Poliovirus), Poxviridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), or any combination thereof. In another embodiment of the disclosure, the viral infection is caused by a virus selected from the group consisting of herpes, pox, papilloma, corona, influenza, hepatitis, sendai, sindbis, vaccinia viruses, west nile, hanta, or viruses which cause the common cold. In another embodiment of the disclosure, the virus is coronavirus (CoV), human immunodeficiency virus, or Orthomyxoviridae. Particularly, the virus is alpha-CoV, beta-CoV, gamma-CoV, or delta-CoV.

The term "coronavirus" or "CoV" refers to any virus of the coronavirus family, including but not limited to SARS-CoV-2, MERS-CoV, and SARS-CoV. SARS-CoV-2 refers to the newly-emerged coronavirus which is rapidly spreading to other areas of the globe. It binds via the viral spike protein to human host cell receptor angiotensin-converting enzyme 2 (ACE2).

In some embodiments of the disclosure, the antibody is a monoclonal antibody, a mammalian antibody, a recombinant mammalian antibody, a humanized antibody, a human antibody, an antibody Fab fragment, F(ab')$_2$, Fv fragment or Fc fragment from a cleaved antibody, a scFv-Fc fragment, a minibody, a diabody, or a scFv.

The antibody described herein also includes an antigen-binding fragment of a full antibody molecule. An antigen-binding fragment of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of an antigen-binding fragment include: (i) Fab fragments; (ii) F(ab')$_2$ fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody typically comprises at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_{H1}$; (ii) $V_H$-$C_{H2}$; (iii) $V_H$-$C_{H3}$; (iv) $V_H$-$C_{H1}$-$C_{H2}$; (v) $V_H$-$C_{H1}$-$C_{H2}$-$C_{H3}$, (vi) $V_H$-$C_{H2}$-$C_{H3}$; (vii) $V_H$-$C_L$; (viii) $V_L$-$C_{H1}$; (ix) $V_L$-$C_{H2}$; (x) $V_L$-$C_{H3}$; (xi) $V_L$-$C_{H1}$-$C_{H2}$; (xii) $V_L$-$C_{H1}$-$C_{H2}$-$C_{H3}$; (xiii) $V_L$-$C_{H2}$-$C_{H3}$; and (Xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with a full antibody molecule, an antigen-binding fragment may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

Preferably, the glycoengineered antibody or antigen-binding fragment thereof according to the disclosure is a mammalian antibody.

The term "mammalian antibody", as used herein, is intended to include antibodies having variable and constant regions derived from mammalian germline immunoglobulin sequences. The mammalian antibodies of the disclosure may include amino acid residues not encoded by mammalian germline immunoglobulin sequences (e.g., mutations introduced by random or site-specific mutagenesis in vitro or by somatic mutation in vivo), for example in the CDRs and in particular CDR3.

The term "recombinant mammalian antibody", as used herein, is intended to include all mammalian antibodies that are prepared, expressed, created or isolated by recombinant means, such as antibodies expressed using a recombinant expression vector transfected into a host cell (detailed as follows), antibodies isolated from a recombinant, combinatorial mammalian antibody library (detailed as follows), antibodies isolated from an animal (e.g., a mouse) that is transgenic for mammalian immunoglobulin genes or antibodies prepared, expressed, created or isolated by any other means that involves splicing of mammalian immunoglobulin gene sequences to other DNA sequences. Such recombinant mammalian antibodies have variable and constant regions derived from mammalian germline immunoglobulin sequences. In certain embodiments, however, such recombinant mammalian antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the mammalian antibody germline repertoire in vivo.

Mammalian antibodies such as human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The antibody disclosed herein comprises one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes an antibody, and an antigen-binding fragment thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another mammalian germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, could easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework(s) and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present disclosure.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Preferably, the antibody according to the disclosure is a monoclonal antibody.

The antibodies of the present disclosure may be monospecific, bi-specific, or multispecific. Multispecific antibodies may be specific for different epitopes of one target polypeptide or may contain antigen-binding domains specific for more than one target polypeptide. The anti-α-toxin antibodies of the present disclosure can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present disclosure includes bi-specific antibodies wherein one arm of an immunoglobulin is specific for the antigen, and the other arm of the immunoglobulin is specific for a second therapeutic target or is conjugated to a therapeutic moiety.

In some embodiments of the disclosure, the antibody CR3022 or antigen-binding fragment thereof comprises a heavy chain variable region comprising the amino acid sequence of SEQ ID NO: 2 or a substantially similar sequence thereof having at least 90%, at least 95%, at least 98% or at least 99% sequence identity; and a light chain variable region comprising the amino acid sequence of SEQ ID NO: 3 or a substantially similar sequence thereof having at least 90%, at least 95%, at least 98% or at least 99% sequence identity.

The glycoengineered antibody or antigen-binding fragment thereof according to the disclosure has a glycoengineered Fc. As used herein, the term "glycoengineered Fc" refers to N-glycan on the Fc region that has been altered or engineered either enzymatically or chemically. The term "Fc glycoengineering" as used herein refers to the enzymatic or chemical process used to make the glycoengineered Fc.

The glycoengineered antibody or antigen-binding fragment thereof according to the present disclosure is a glycoantibody. The term "glycoantibody" as used herein refers to a homogeneous population of monoclonal antibodies having a single, uniform glycoform on Fc region. The individual glycoantibodies8 in the homogeneous population are identical, bind to the same epitope, and contain the same Fc glycan with a well-defined glycan structure and sequence.

The term "homogeneous" in the context of a glycosylation profile of Fc region is intended to mean a single glycosylation pattern represented by one desired N-glycan species, with little or no trace amount of precursor N-glycan. In certain embodiments, the purity of Fc with the desired N-glycan is greater than about 85%. In certain embodiments, the purity of Fc with the desired N-glycan is greater than about 90%. In certain embodiments, the purity of Fc with the desired N-glycan is greater than about 95%.

As used herein, the term "glycan" refers to a polysaccharide, oligosaccharide or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of O-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is an Asn-X-Ser or Asn-X-Thr sequence, where X is any amino acid except proline.

As used herein, the term "N-glycan" refers to an N-linked oligosaccharide attached by an N-acetylglucosamine (GlcNAc) linked to the amide nitrogen of an asparagine residue in an Fc-containing polypeptide.

As disclosed herein, the glycoengineered antibody or antigen-binding fragment thereof has the N-glycan is represented by the general formula (I)

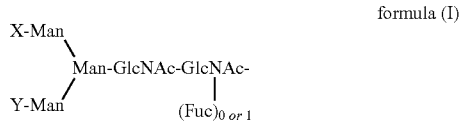

formula (I)

wherein:

each of X and Y presents a glycan, and X and Y are identical.

In some embodiments of the disclosure, each of X and Y presents GlcNAc-, GalGlcNAc-, Sia(α2-3)GalGlcNAc-, or Sia(α2-6)GalGlcNAc-.

In some embodiments of the disclosure, the N-glycan is selected from the group consisting of $GlcNAc_2Man_3GlcNAc_2(Fuc)$ (G0F), $GlcNAc_2Man_3GlcNAc_2$ (G0), $Gal_2GlcNAc_2Man_3GlcNAc_2$ (Fuc) (G2F), $Gal_2GlcNAc_2Man_3GlcNAc_2$ (G2), $Sia_2(\alpha 2\text{-}3)Gal_2GlcNAc_2Man_3GlcNAc_2(Fuc)$ (G2S2F (alpha 2,3 linkage)), $Sia_2(\alpha 2\text{-}6)Gal_2GlcNAc_2Man_3GlcNAc_2(Fuc)$ (G2S2F (alpha 2,6 linkage)), $Sia_2(\alpha 2\text{-}6)Gal_2GlcNAc_2Man_3GlcNAc_2$ (G2S2 (alpha 2,6 linkage)), and $Sia_2(\alpha 2\text{-}3)Gal_2GlcNAc_2Man_3GlcNAc_2$ (G2S2 (alpha 2,3 linkage)), and a plurality of the antibodies or antigen-binding fragment thereof are provided in a population, and more than about 90% of the population has the same N-glycan. The schematic structures of the N-glycan are shown in FIG. 1. In some embodiments of the disclosure, the N-glycan is selected from the group consisting of G2F, G2, G2S2F (alpha 2,3 linkage), G2S2F (alpha 2,6 linkage), and G2S2 (alpha 2,6 linkage).

In some embodiments of the disclosure, the ratio of the antigen portion to the glycoengineered antibody or antigen-binding fragment thereof ranges from 1:10 to 10:1, such as 1:10, 1:9, 1:8, 1:7, 1:6, 1:5, 1:4, 1:3, 1:2, 1:1, 2:1, 3:1, 4:1, 5:1, 6:1, 7:1, 8:1, 9:1 and 10:1.

In another aspect, the present disclosure also provides an immune combination comprising an effective amount of the composition comprising the glycoengineered antibody or antigen-binding fragment thereof as disclosed herein and pharmaceutically acceptable carrier and/or adjuvant.

The present disclosure also provides a method for treating an infection by a virus in a subject in need of such treatment comprising administering the composition or immune combination as disclosed herein to the subject.

The composition or immune combination as disclosed herein is surprised to show an excellent ability to induce a superior immune response when compared to comparative compositions or immune combinations comprising a non-glycoengineered antibody or antibody not defined in formula (I) such as X and Y are different. The symmetric N-glycan induces the superior immune response. In some embodiments of the disclosure, the composition or immune combination comprising the glycoengineered antibody or antigen-binding fragment thereof having the symmetric glycan as disclosed herein induces a higher level of high-avidity antibodies specific to the virus and/or elicits robust broadly neutralizing antibodies against the virus.

As used herein, the term "combination", or "immune combination", as used herein, defines either a fixed combination in one dosage unit form or a kit of parts for the combined administration where Compound A and Compound B may be administered independently at the same time or separately within time intervals.

As used herein, the term "effective amount" refers to the amount of an agent that, when administered to a mammal or other subject for treating a disease, is sufficient to effect such treatment for the disease.

As used herein, the terms "treatment," "treating," and the like, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

As interchangeably used herein, the terms "individual," "subject," "host," and "patient," refer to a mammal, including, but not limited to, murines (rats, mice), non-human primates, humans, canines, felines, ungulates (e.g., equines, bovines, ovines, porcines, caprines), etc.

As used herein, the term "in need of treatment" refers to a judgment made by a caregiver (e.g., physician, nurse, nurse practitioner, or individual in the case of humans; veterinarian in the case of animals, including non-human mammals) that a subject requires or will benefit from treatment. This judgment is made based on a variety of factors that are in the realm of a caregiver's expertise, but that includes the knowledge that the subject is ill, or will be ill, as the result of a condition that is treatable by the compounds of the present disclosure.

The immune combination of the disclosure are formulated with suitable diluents, carriers, excipients, and other agents that provide improved transfer, delivery, tolerance, and the like. The immune combination may be formulated for specific uses, such as for veterinary uses or pharmaceutical uses in humans. The form of the composition and the excipients, diluents and/or carriers used will depend upon the intended uses of the antibody and, for therapeutic uses, the mode of administration. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water, and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present disclosure is used for treating viral infection in an adult patient, it may be advantageous to intravenously administer the antibody of the present disclosure. Depending on the severity of the condition, the frequency and the duration of the treatment can be adjusted. Effective dosages and schedules for administering the antibody may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the immune combination of the disclosure, e.g., encapsulation in liposomes, microparticles, microcapsules, recombinant cells capable of expressing the mutant viruses, receptor-mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The immune combination may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local.

The immune combination of the present disclosure can be delivered subcutaneously or intravenously with a standard needle and syringe. In addition, with respect to subcutaneous delivery, a pen delivery device readily has applications in delivering an immune combination of the present disclosure. Such a pen delivery device can be reusable or disposable. A reusable pen delivery device generally utilizes a replaceable cartridge that contains an immune combination. Once all of the immune combination within the cartridge has been administered and the cartridge is empty, the empty cartridge can readily be discarded and replaced with a new cartridge that contains the immune combination. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the immune combination can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending, or emulsifying the antibody described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the immune combination for oral or parenteral use as described can be prepared into dosage forms in a unit dose suited to fit a dose of the active ingredients. Such dosage forms in a unit dose include, for example, tablets, pills, capsules, injections (ampoules), suppositories, etc.

In some embodiments of the disclosure, the method is for neutralizing the virus and/or enhancing antibody-dependent cell-mediated cytotoxicity in the subject.

"Neutralizing" refers to a process in which a molecule (e.g. antibody) inhibits an activity of a coronavirus to any detectable degree.

As illustrated in the Examples, animals immunized with the compositions or immune combinations according to the disclosure show a comparable or higher level of serum IgG antibodies, especially IgG1 antibodies, as comparing to mice immunized with the antigen and non-glycoengineered antibody. Furthermore, the composition or immune combination according to the disclosure is able to induce a more balanced Th1/Th2 responses and high-avidity antibodies. A two-dose regimen of the composition or immune combination can elicit robust broadly neutralizing antibodies against not only wild type virus, but also various mutant variants. In contrast, the virus neutralization activity of antibodies elicited by the antigen and non-glycoengineered antibody is significantly compromised. Moreover, the composition or immune combination according to the disclosure shows a higher neutralization activity.

In some embodiments of the disclosure, the immune combination further comprises a vaccine of the virus. In another aspect, the method comprises co-administering the composition or immune combination and the vaccine of the virus. In some embodiments of the disclosure, the vaccine comprises the antigen portion.

As used herein, the term "co-administration" or "combined administration" is intended to encompass the administration of the selected therapeutic agents to a single patient, and include treatment regimens in which the agents are not necessarily administered by the same route of administration or at the same time. In some embodiments of the disclosure, the immune combination further comprises a vaccine of the virus, and the vaccine is administered prior to the composition or immune combination.

The composition and the antigen portion may be co-administered simultaneously, separately or sequentially or co-administered in combination as a coformulation.

The co-administration may include simultaneous administration of the composition and the antigen portion and optionally the vaccine in the same or different dosage form, or separate administration of the therapeutic agents. For example, the composition and the antigen portion and optionally the vaccine may be simultaneously administered. Alternatively, the composition and the antigen portion and optionally the vaccine are formulated for separate administration and are administered concurrently or sequentially.

In some embodiments of the disclosure, the method comprises administering the composition at least two times. In some embodiments of the disclosure, the method is for priming and subsequently boosting an immune response at different times. For example, the method comprises: (i) administering at least one dose of a priming immunogenic composition to the subject, to elicit a primary immune response; and (ii) administering a boosting immunogenic composition to the subject, to elicit, within 7, 10, 12, 14, 15, 18, 20, 21, 25, 28, 30, 35, 40, 42, 49, 50 days of its administration or sooner, a protective anamnestic immune response.

As illustrated in the Examples, heterologous prime-boost of the antigen portion and the composition induce a significantly higher titer than two doses of the antigen only. Similarly, two doses of antigen, boosting with one additional dose of the composition according to the disclosure significantly improved the serum IgG titer.

The following examples are provided to aid those skilled in the art in practicing the present disclosure.

EXAMPLES

Example 1 Methods of Preparing Glyco-Engineering CR3022 (CHOptimax™)

Materials for Glyco-Engineering CR3022

Enzyme-A: EndoS2$^{T138E}$ or EndoS2$^{D184M}$
Enzyme-B: EndoS2$^{T138Q}$-Alfc or EndoS2$^{D184M}$-Alfc
Sugar-A: Gal$_2$GlcNAc$_2$Man$_3$GlcNAc-oxazoline (CT-ox)
Sugar-B: Sia($\alpha$2-6)Gal$_2$GlcNAc$_2$Man$_3$GlcNAc-oxazoline (2,6-mono-Sia-CT-ox)
Sugar-C: Sia$_2$($\alpha$2-6)Gal$_2$GlcNAc$_2$Man$_3$GlcNAc-oxazoline (2,6-SCT-ox)
Sugar-D: Sia$_2$($\alpha$2-3)Gal$_2$GlcNAc$_2$Man$_3$GlcNAc-oxazoline (2,3-SCT-ox)
Sugar-E: GlcNAcMan$_3$GlcNAc-oxazoline
Sugar-F: GlcNAc$_2$Man$_3$GlcNAc-oxazoline
Sugar-G: GalGlcNAc$_2$Man$_3$GlcNAc-oxazoline General Protocol of Glyco-Engineering CR3022

CR3022 was treated with enzyme in Tris-HCl (pH 7.0) buffer on 37° C. for 16 hours. And then the temperature of reaction solution was adjusted to 30° C. The sugar was dissolved by water, and then added into the reaction solution. After shaking for 30 minutes, the reaction solution was filtered by 0.2 μm filter, and further purified by MabSelect resin to obtain CR3022 with desired glyco-form as shown in Table 1.

TABLE 1

Glyco-engineered CR3022, prepared by CHOptimax ™

|  | Enzyme-A | Enzyme-B |
|---|---|---|
| Sugar-A (CT-ox) | CR3022-G2F | CR3022-G2 |
| Sugar-B (2,6-mono-Sia-CT-ox) | CR3022-G2S1F ($\alpha$2-6) | CR3022-G2S1 ($\alpha$2-6) |
| Sugar-C (2,6-SCT-ox) | CR3022-G2S2F ($\alpha$2-6) | CR3022-G2S2 ($\alpha$2-6) |
| Sugar-D (2,3-SCT-ox) | CR3022-G2S2F ($\alpha$2-3) | CR3022-G2S2 ($\alpha$2-3) |
| Sugar-E | CR3022-G0F-N |  |
| Sugar-F | CR3022-G0F | CR3022-G0 |
| Sugar-G | CR3022-G1F |  |

Figure 2:
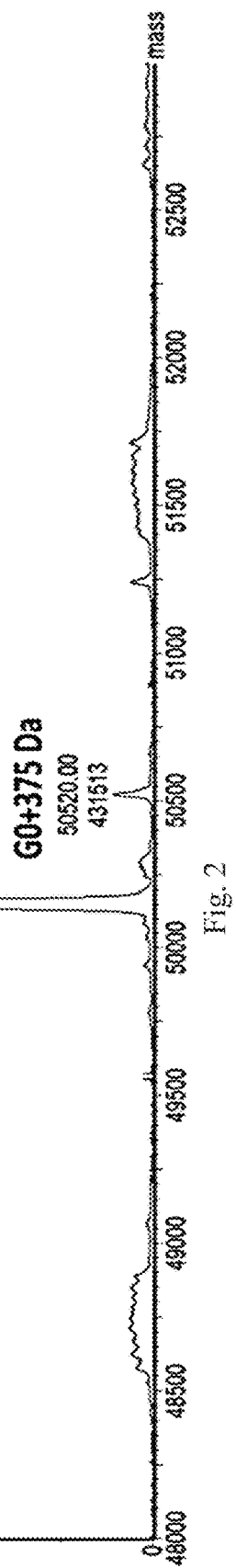
FIG. 2 shows the results of mass analyses of glycoengineered CR3022.
Figure 2:
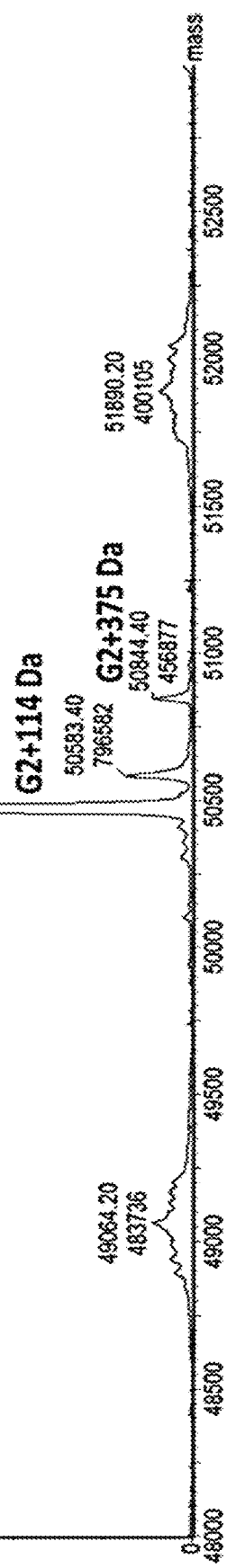
Figure 2:
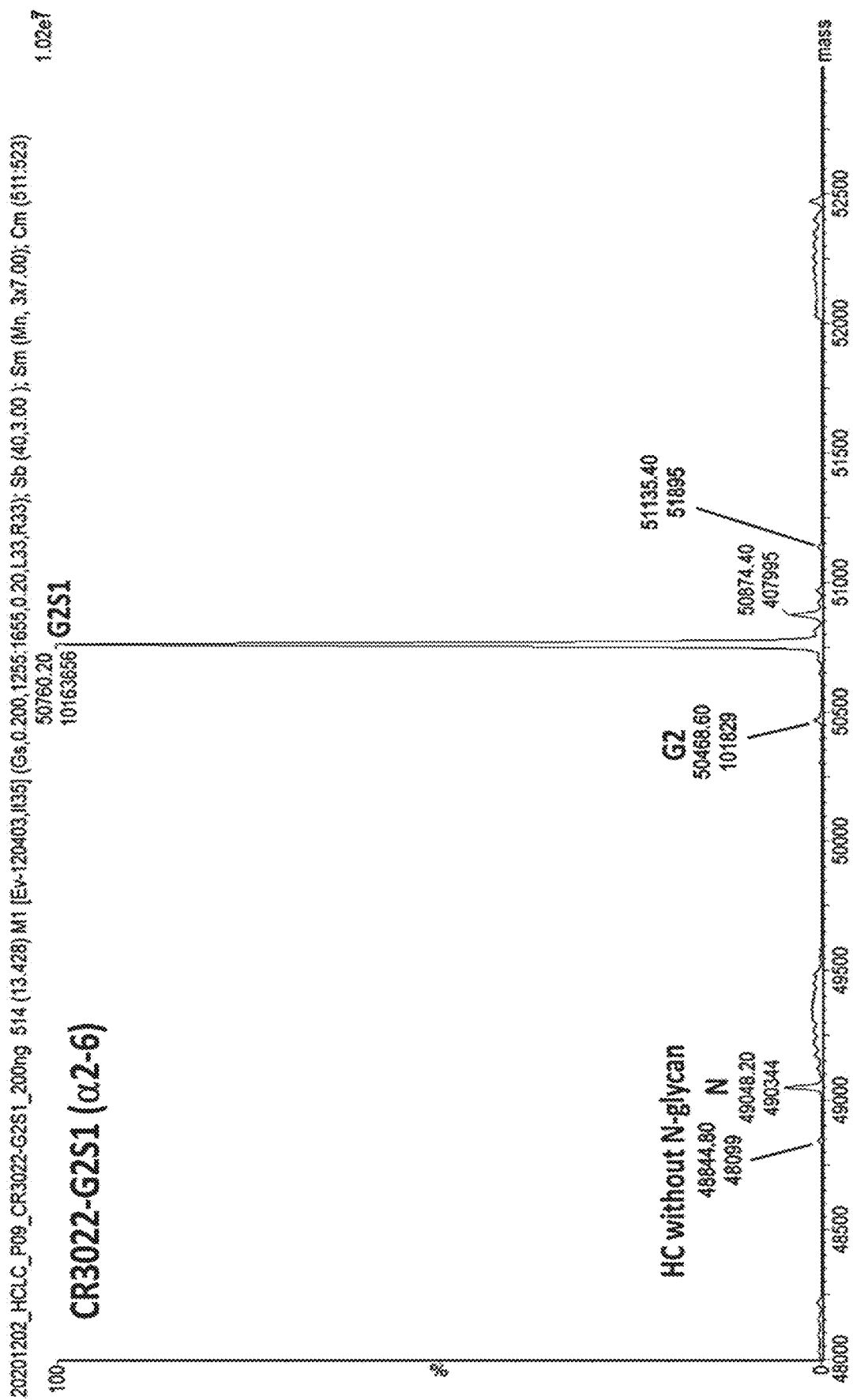
Figure 2:
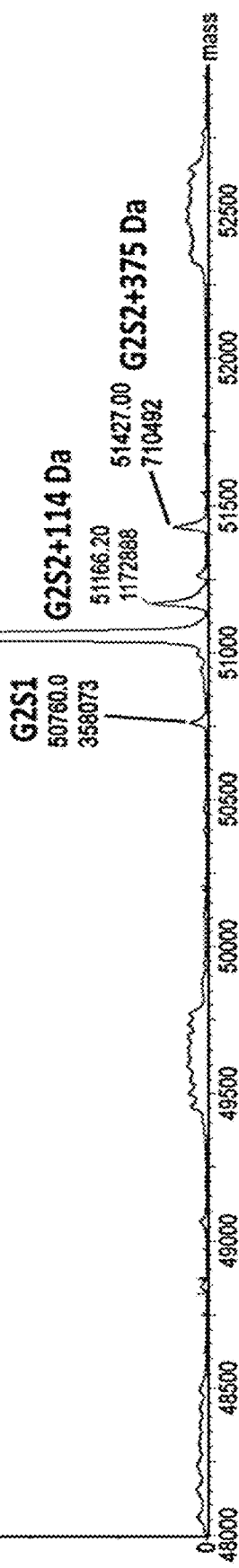
Figure 2:
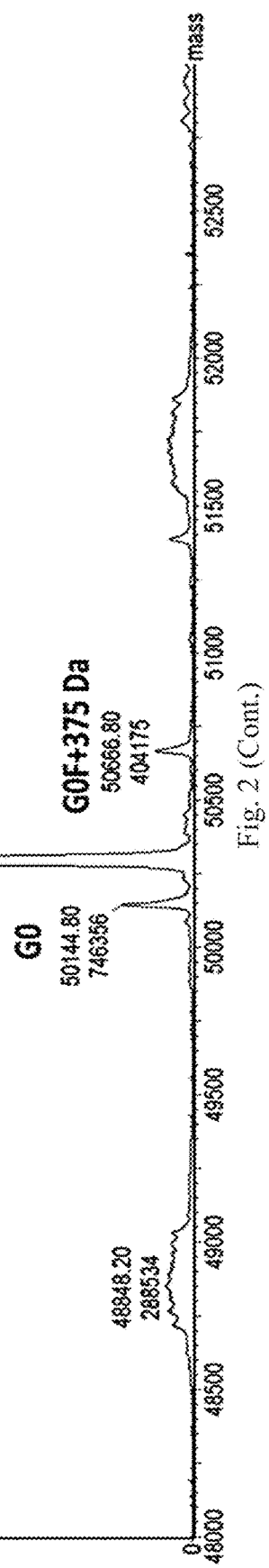
Figure 2:
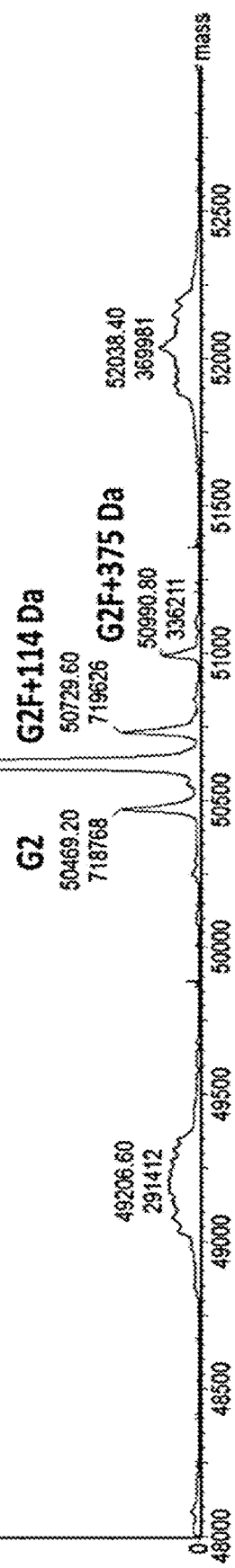
Figure 2:
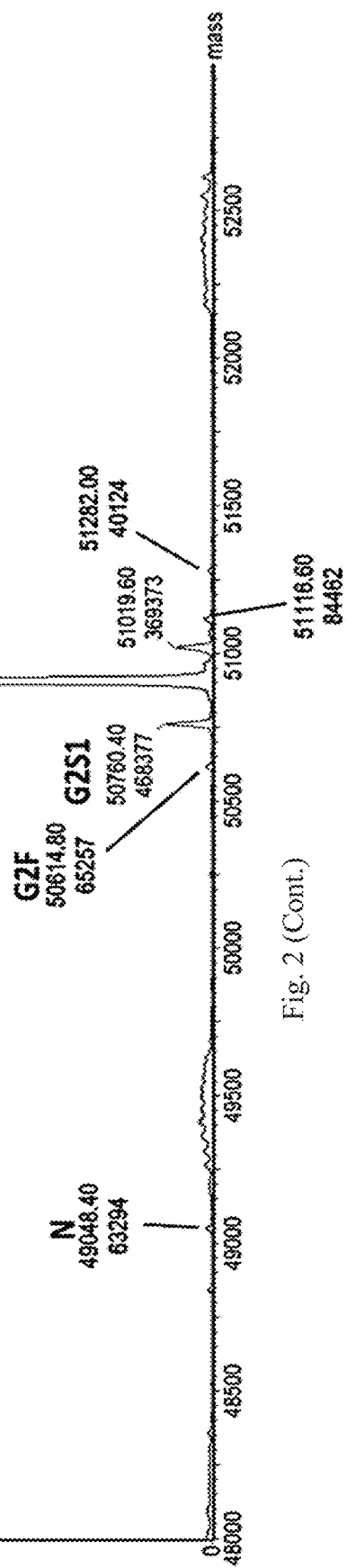
Figure 2:
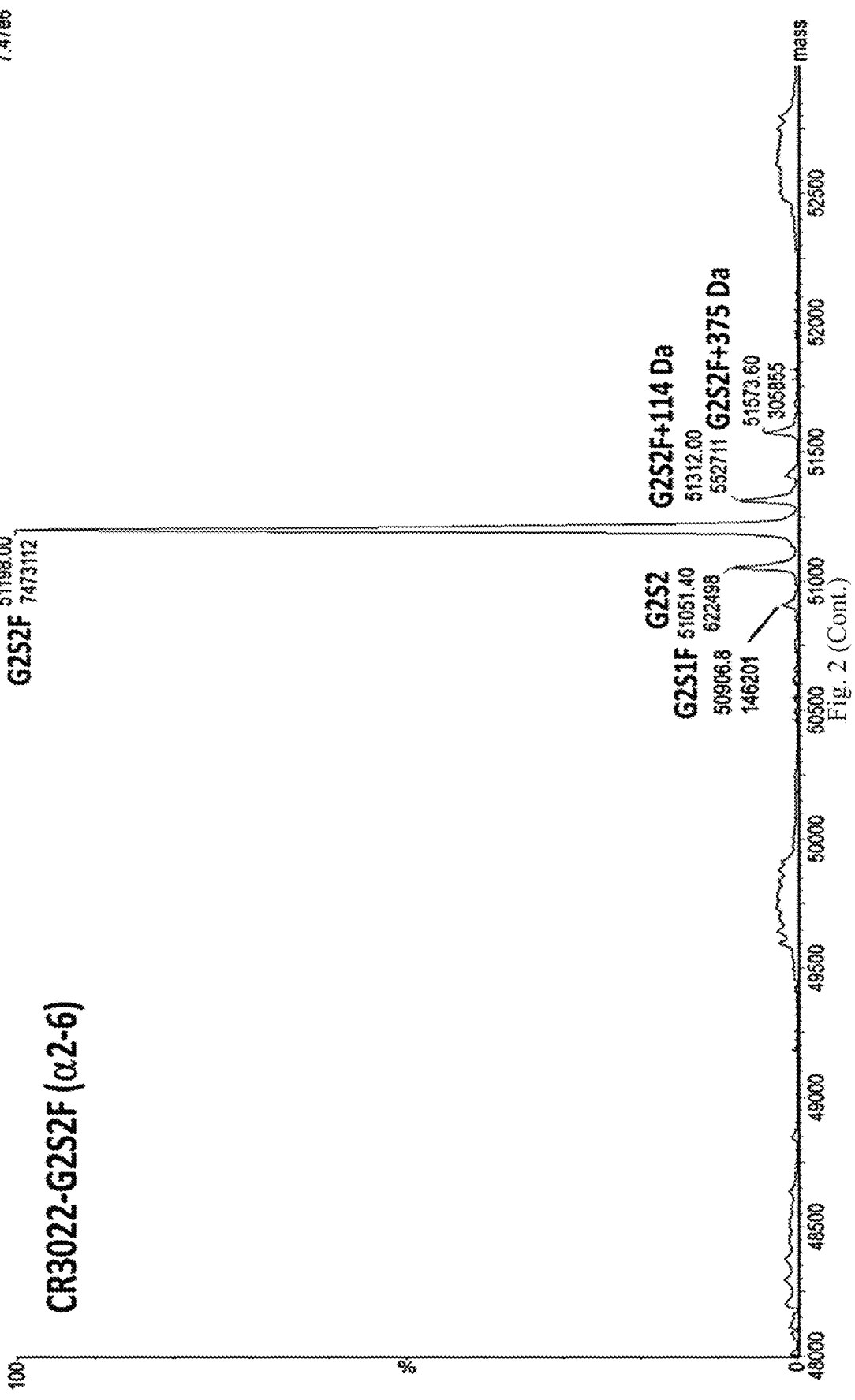
Figure 2:
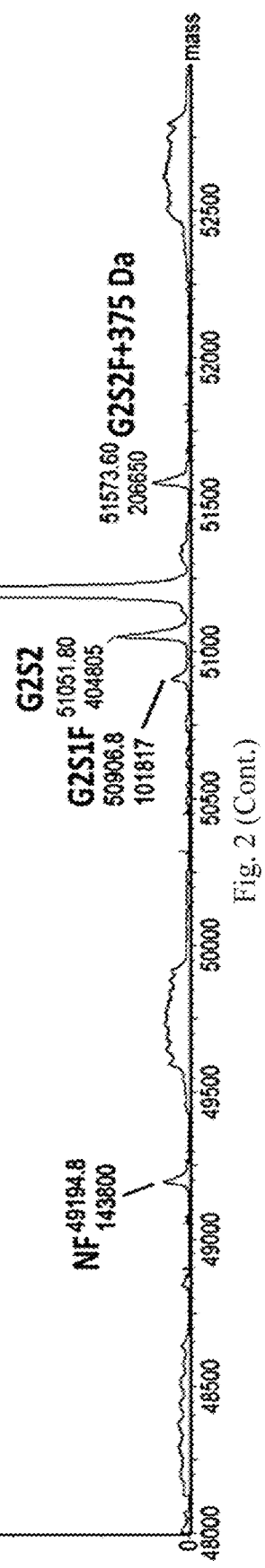

The glyco-form of engineered CR3022 were confirmed by mass analyses and shown in FIG. 2 and Table 2.

TABLE 2

Heavy Chain Mass of Glycan-engineered CR3022

| Antibody | Molecular Weight |
|---|---|
| CR3022-G0 | 50144.80 |
| CR3022-G2 | 50469.40 |
| CR3022-G2S1 ($\alpha$2-6) | 50760.20 |
| CR3022-G2S2 ($\alpha$2-6) | 51051.40 |
| CR3022-G0F | 50291.00 |
| CR3022-G2F | 50615.20 |
| CR3022-G2S1F ($\alpha$2-6) | 50906.40 |
| CR3022-G2S2F ($\alpha$2-6) | 51198.00 |
| CR3022-G2S2F ($\alpha$2-3) | 51198.20 |

The glycoforms (%) of CR3022 and its glycoengineered variants are shown in Table 3.

TABLE 3

|  |  | Original | G2F | G2 | G2S1F ($\alpha$2, 6) | G2S2F ($\alpha$2, 3) | G2S2F ($\alpha$2, 6) | G2S2 ($\alpha$2, 3) |
|---|---|---|---|---|---|---|---|---|
| Glycoforms (%) | N$^1$ | 0 | 0 | 0 | 0.7 | 0 | 0 | 0 |
|  | NF$^2$ | 0 | 0 | 0 | 0 | 2.5 | 0 | 0 |
|  | Man5 | 4.8 | 0 | 0 | 0 | 0 | 0 | 0 |
|  | G0F-N$^3$ | 3.7 | 0 | 0 | 0 | 0 | 0 | 0 |
|  | G0F | 57.5 | 0 | 0 | 0 | 0 | 0 | 0 |
|  | G0 | 0 | 0 | 0 | 0 | 0 | 0 | 0 |
|  | G1F | 29.4 | 0 | 0 | 0 | 0 | 0 | 0 |
|  | G2F | 4.6 | 92.8 | 0 | 0.7 | 0 | 0 | 0 |
|  | G2 | 0 | 7.2 | 100 | 0 | 0 | 0 | 0 |
|  | G2S1F | 0 | 0 | 0 | 93.8 | 1.8 | 1.6 | 0 |

TABLE 3-continued

|  | Original | G2F | G2 | G2S1F (α2, 6) | G2S2F (α2, 3) | G2S2F (α2, 6) | G2S2 (α2, 3) |
|---|---|---|---|---|---|---|---|
| G2S1 | 0 | 0 | 0 | 4.8 | 0 | 0 | 1.7 |
| G2S2F | 0 | 0 | 0 | 0 | 88.8 | 91.6 | 0 |
| G2S2 | 0 | 0 | 0 | 0 | 6.9 | 6.8 | 98.3 |

[1]"N" means mono-GlcNAc; [2]"NF" means mono-GlcNAc with fucose; [3]"G0F-N" means G0F minuses a terminal GlcNAc

Example 2 Glycoengineered Compositions or Immune Combinations can Elicit Robust IgG Titer Against SARS-CoV-2 RBD Pathogen-free BALB/c mice (female, 6-week-old from BioLASCO) were used for vaccination study. SARS-CoV-2 RBD (10 μg) was delivered alone intramuscularly, or in complex with original or glycoengineered CR3022 at a molar ratio of 1:1 (Ag:Ab). All vaccines were adjuvanted with Adju-Phos (InvivoGen) and the final volume was brought to 100 μL with PBS, pH7.4 for each injection. Mice were primed and boosted via intramuscular injection at Day 1 and Day 21, respectively. Ten days after the boosting, mice were sacrificed and the blood was collected for ELISA and virus neutralization assays.

ELISA was conducted to determine the serum total IgG titer of anti-SARS-CoV-2 RBD antibodies. Briefly, 200 ng of SARS-CoV-2 RBD (2 μg/mL) was coated on the wells of 96-well ELISA plate. After blocking with 1% BSA, 100 μL of the diluted mouse serum (5,000× in PBS) was added into the well and allowed to incubate for 2 hours at room temperature. Following the wash cycle (with 0.05% Tween-20/PBS), HRP-conjugated anti-mouse IgG-specific antibody was applied for detection.

Figure 3:
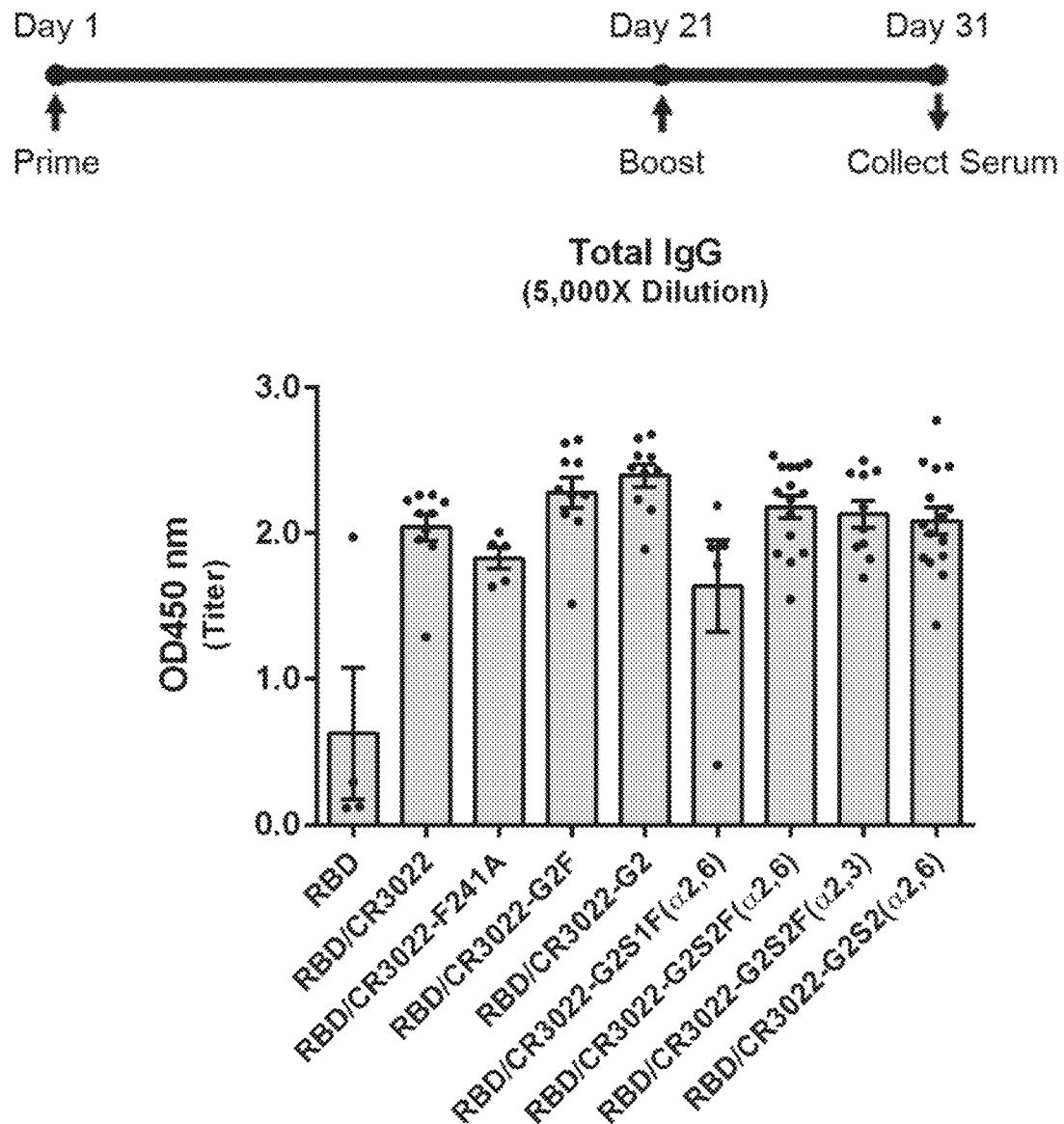
FIG. 3 shows the results of serum titer against SARS-CoV-2 RBD by ELISA of Example 2.

The results are shown in FIG. 3. Mice immunized with SARS-CoV-2 RBD alone showed the lowest serum IgG titer against RBD, as comparing to other groups. Mice immunized with immune complexes comprising RBD plus CR3022-F241A (Alanine point mutation at residue F241 without glycoengineering) and RBD plus CR3022-G2S1F (alpha 2,6) showed a lower level of serum IgG titer against RBD, as comparing to mice immunized with RBD/original CR3022. And mice immunized with immune complexes comprising RBD plus glycoengineered CR3022 variants, including G2F, G2, G2S2F (either alpha 2,3- or alpha 2,6-), and G2S2 (alpha 2,6-), showed a comparable or higher level of serum anti-RBD IgG antibodies, as comparing to mice immunized with RBD/original CR3022.

Example 3 Glycoengineered Compositions or Immune Combinations can Induce IgG Subclass Switching The immunization was as shown in Example 2.

ELISA was conducted to determine the subclass of the induced anti-SARS-CoV-2 RBD IgG antibodies. Briefly, 200 ng of SARS-CoV-2 RBD (2 μg/mL) was coated on the wells of 96-well ELISA plate. After blocking with 1% BSA, 100 μL of the diluted mouse serum (1,000× in PBS) was added into the well and allowed to incubate for 2 hours at room temperature. Following the wash cycle (with 0.05% Tween-20/PBS), HRP-conjugated anti-mouse IgG subclass-specific antibody was applied for detection.

Figure 4:
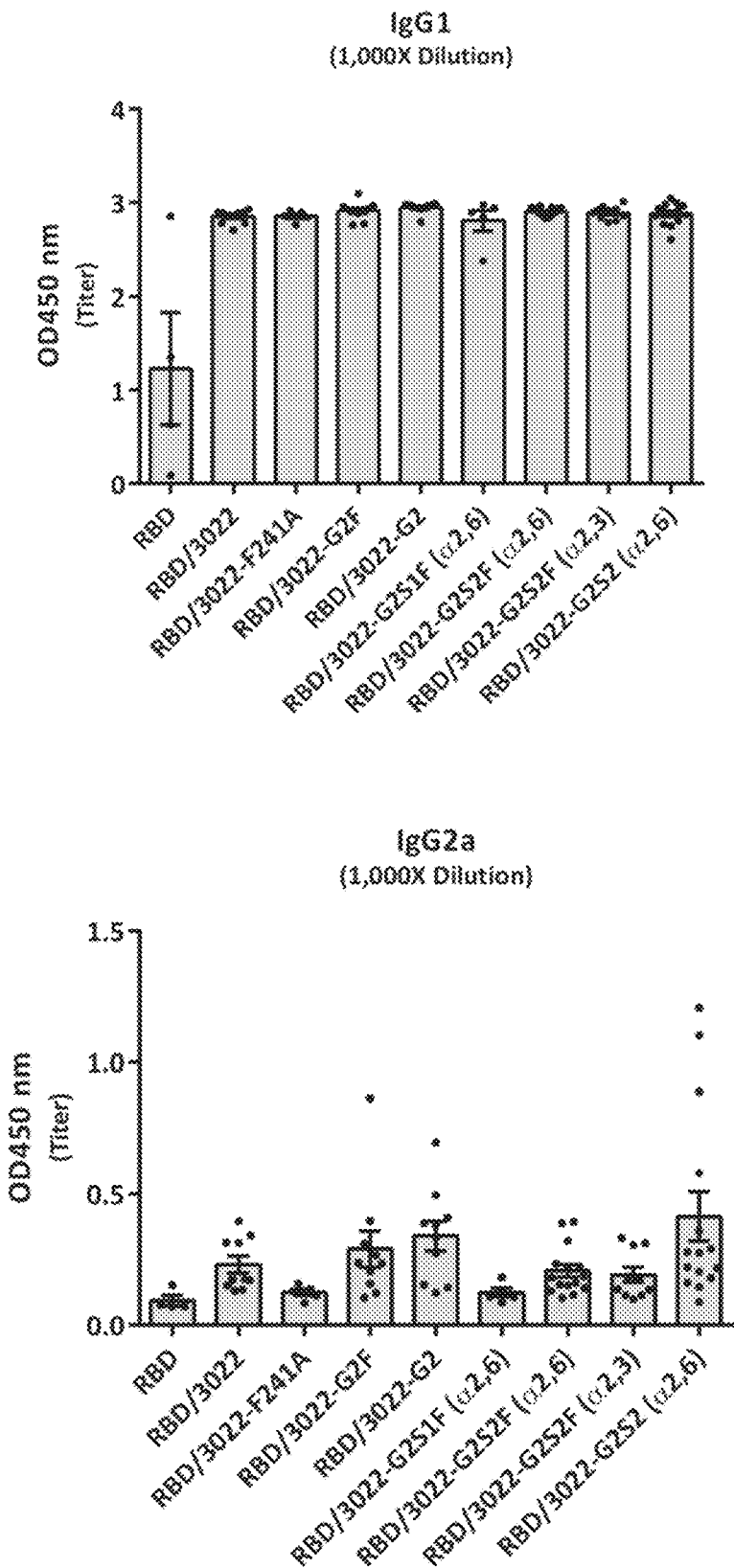
FIG. 4 shows the results of serum titer against SARS-CoV-2 RBD by ELISA of Example 3.
Figure 4:
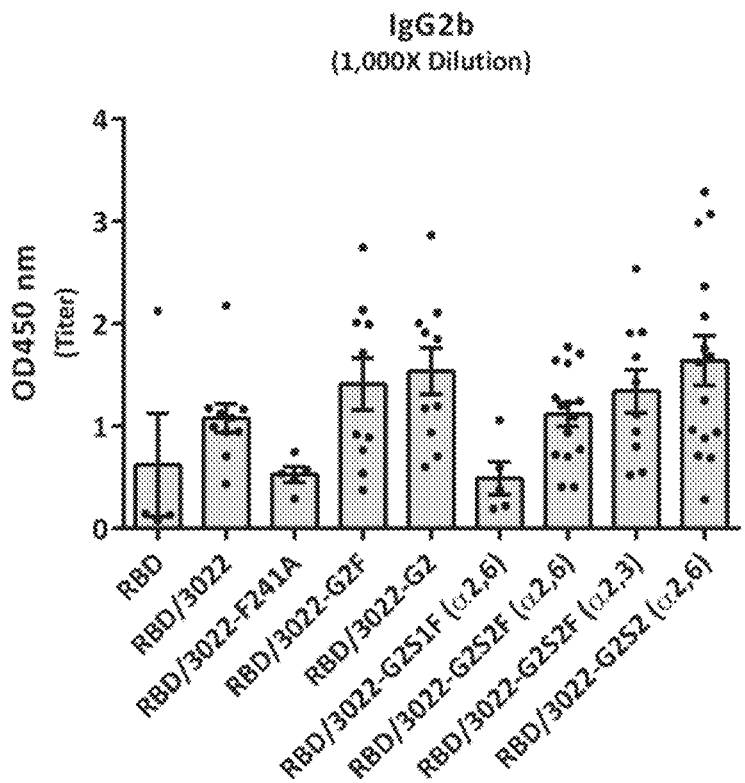
Figure 4:
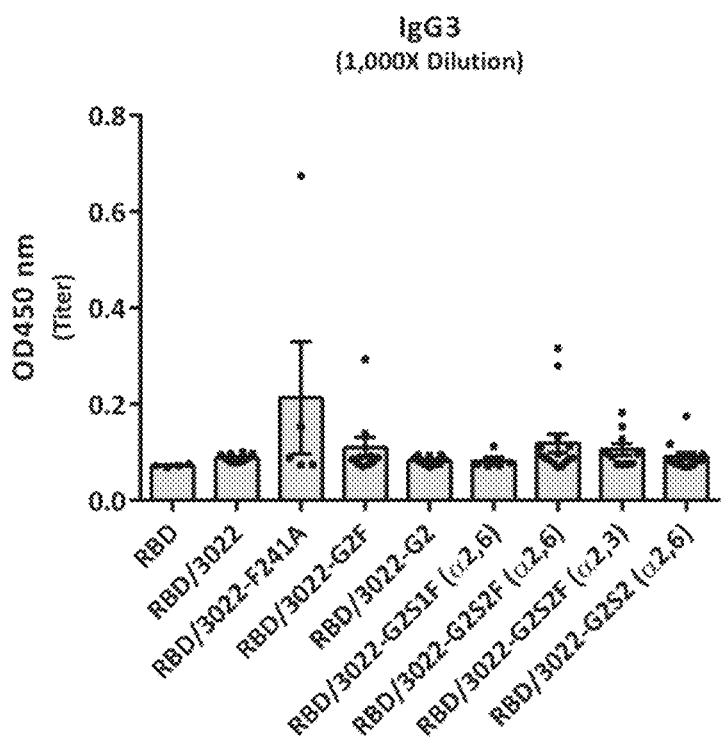

The results as illustrated in FIG. 4 and Table 4 show that the all-immunized mice, except the group of mice received SARS-CoV-2 RBD alone, showed a comparable level of anti-RBD IgG1 antibodies. Interestingly, as comparing to mice immunized with RBD/original CR3022, mice immunized with RBD plus glycoengineered CR3022 variants, including G2, G2F, G2S2F (either alpha 2,3- or alpha 2,6-), and G2S2 (alpha 2,6-) showed a higher level of anti-RBD IgG2a or IgG2b antibodies. These results suggested that immune complex vaccine comprising RBD and CR3022 antibody with certain glycoforms, including G2, G2F, G2S2F (either alpha 2,3- or alpha 2,6-), and G2S2 (alpha 2,6-), can induce a more balanced Th1/Th2 response, as comparing to other compositions. Only trace level of anti-RBD IgG3 antibodies was detected in all groups.

TABLE 4

|  | Serum dilution folds | | | | |
|---|---|---|---|---|---|
|  | Total IgG | IgG1 | IgG2a | IgG2b | IgG3 |
|  | | | IgG Classes | | |
|  | 5,000× | 1,000× | 1,000× | 1,000× | 1,000X |
| RBD | 31 | 43 | 39 | 58 | 78 |
| RBD/CR3022 | 100 | 100 | 100 | 100 | 100 |
| RBD/CR3022-F241A | 92 | 100 | 52 | 49 | 233 |
| RBD/CR3022-G2F | 112 | 102 | 126 | 132 | 122 |
| RBD/CR3022-G2 | 118 | 104 | 148 | 143 | 89 |
| RBD/CR3022-G2S1F | 80 | 99 | 52 | 46 | 89 |
| RBD/CR3022-G2S2F (α2,6) | 107 | 102 | 91 | 104 | 133 |
| RBD/CR3022-G2S2F (α2,3) | 104 | 101 | 83 | 125 | 111 |
| RBD/CR3022-G2S2 (α2,6) | 102 | 101 | 178 | 153 | 100 |

Example 4 Antibody Avidity

The immunization was as shown in Example 2.

ELISA was conducted to determine the titer and avidity of anti-SARS-CoV-2 RBD IgG antibodies. To determine the titer of total IgG, 200 ng of SARS-CoV-2 RBD (2 μg/mL) was coated on the wells of 96-well ELISA plate. After blocking with 1% BSA, 100 μL of the diluted mouse serum (1,000× in PBS) was added into the well and allowed to incubate for 2 hours at room temperature. Following the wash cycle (with 0.05% Tween-20/PBS), HRP-conjugated anti-mouse IgG-specific antibody was applied for detection. To further determine the titer of high-avidity antibodies, 7 M urea was added into the wells of 96-well ELISA plate and incubated for 15 minutes at room temperature before the addition of the secondary antibody.

Figure 5:
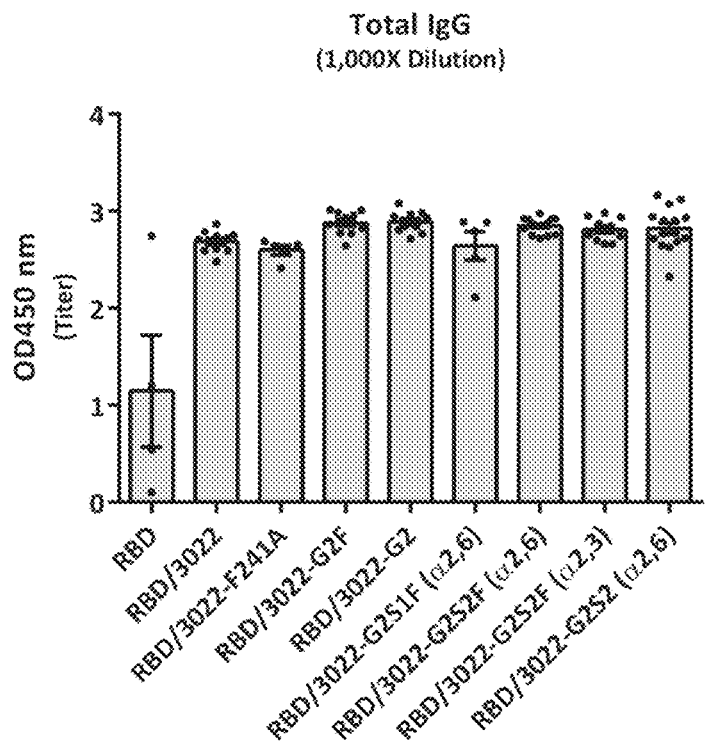
FIG. 5 shows the results of the antibody avidity by ELISA (1000× dilution) of Example 4.

The results showed that the all-immunized mice, except the group of mice received SARS-CoV-2 RBD alone, showed a comparable level of anti-RBD IgG1 antibodies (FIG. 5).

Figure 6:
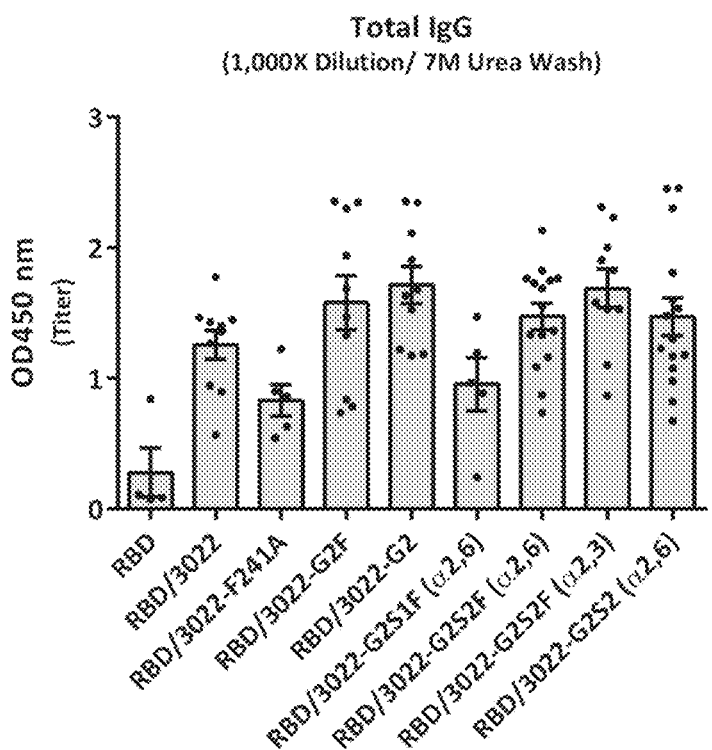
FIG. 6 shows the results of the antibody avidity by ELISA (1000× dilution/7M urea wash) of Example 4.

The 7M urea avidity ELISA was performed to further assess the quality of the induced antibodies. The immune complex vaccines comprising SARS-CoV-2 RBD and glycoengineered CR3022 variants, including G2F, G2, G2S2F (either alpha 2,3- or alpha 2,6-), and G2S2 (alpha 2,6-), can induce a higher level of high-avidity antibodies specific to RBD, as comparing with RBD/original CR3022 immune complex. In contrast, the avidity of antibodies elicited by immune complexes comprising RBD/CR3022-F241A (Alanine point mutation at residue F241) and RBD/CR3022-G2S1F (alpha 2,6) is significantly lower than other immune complex groups (FIG. 6).

Figure 7:
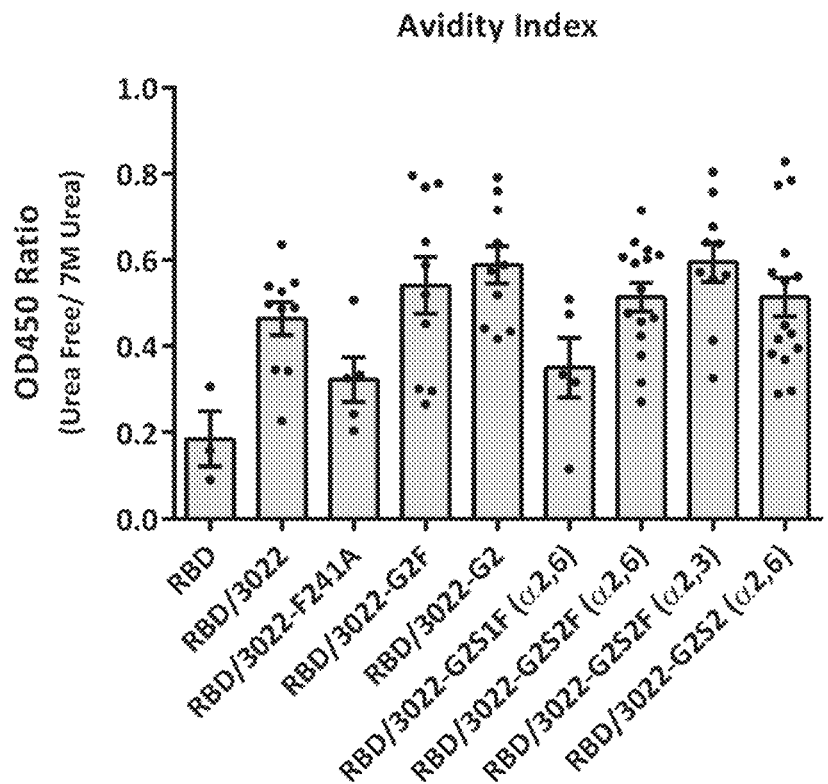
FIG. 7 shows the results of the antibody avidity index by ELISA of Example 4.

The results of avidity index are shown in FIG. 7 and Table 5.

TABLE 5

| | IgG Classes | | |
| --- | --- | --- | --- |
| | | Avidity Index | |
| | Tota IgG | OD450 | % to |
| 7M Urea | $-^a$ | $+^b$ | Ratio (b/a) | RBD/CR3022 |
| RBD | 1.15 | 0.28 | 0.18 | 39 |
| RBD/CR3022 | 2.69 | 1.26 | 0.46 | 100 |
| RBD/CR3022-F241A | 2.60 | 0.83 | 0.32 | 70 |
| RBD/CR3022-G2F | 2.88 | 1.58 | 0.54 | 117 |
| RBD/CR3022-G2 | 2.89 | 1.71 | 0.59 | 128 |
| RBD/CR3022-G2S1F | 2.64 | 0.95 | 0.35 | 76 |
| RBD/CR3022-G2S2F (α2,6) | 2.85 | 1.47 | 0.51 | 111 |
| RBD/CR3022-G2S2F (α2,3) | 2.81 | 1.69 | 0.60 | 130 |
| RBD/CR3022-G2S2 (α2,6) | 2.82 | 1.47 | 0.51 | 111 |

Example 5 Pseudovirus Neutralization

The immunization was as shown in Example 2.

SARS-CoV-2 spike pseudotyped lentivirus with luciferase reporter gene was used for determining the neutralization activities of serum RBD-specific IgGs induced by vaccines.

Figure 8:
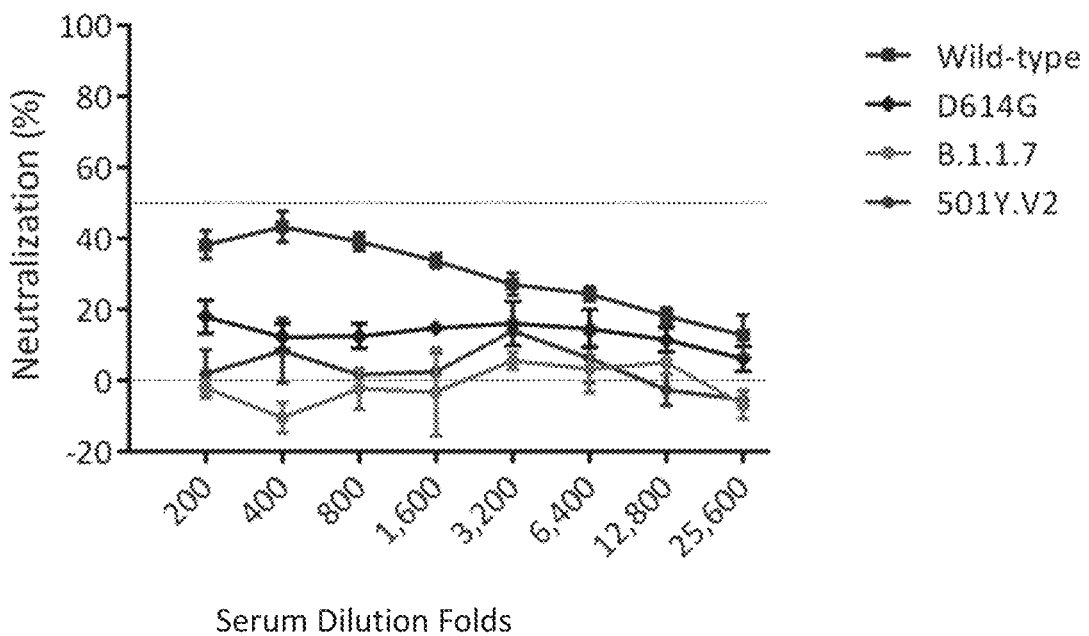
FIG. 8 shows the results of pseudovirus neutralization of Example 5.
Figure 8:
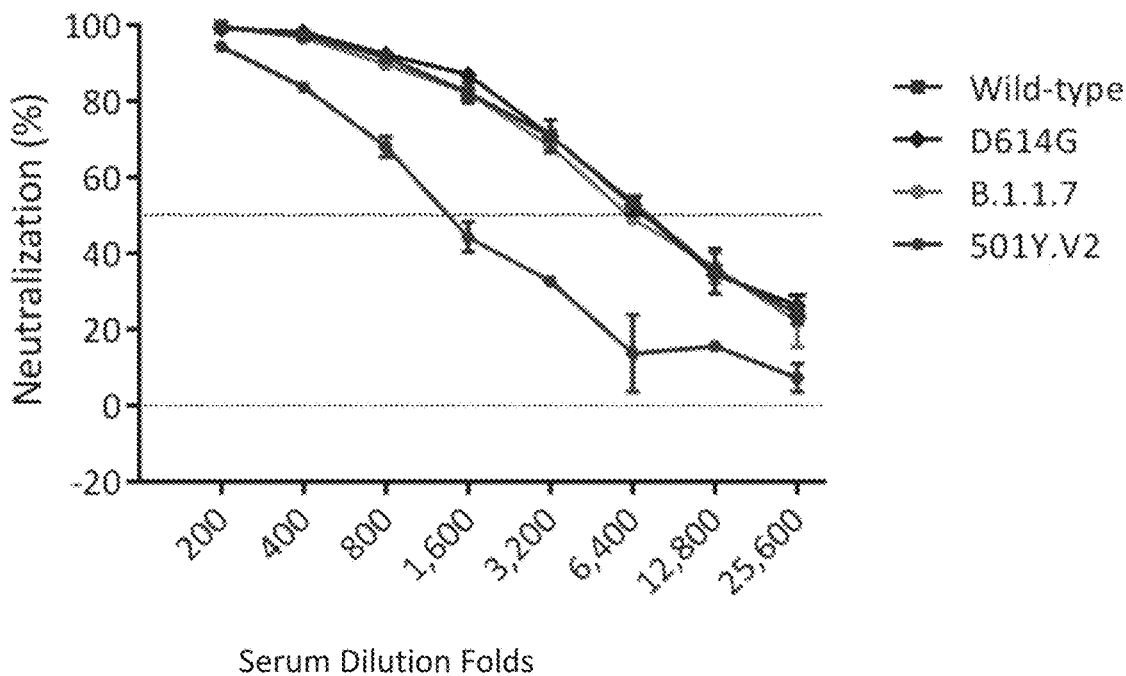
Figure 8:
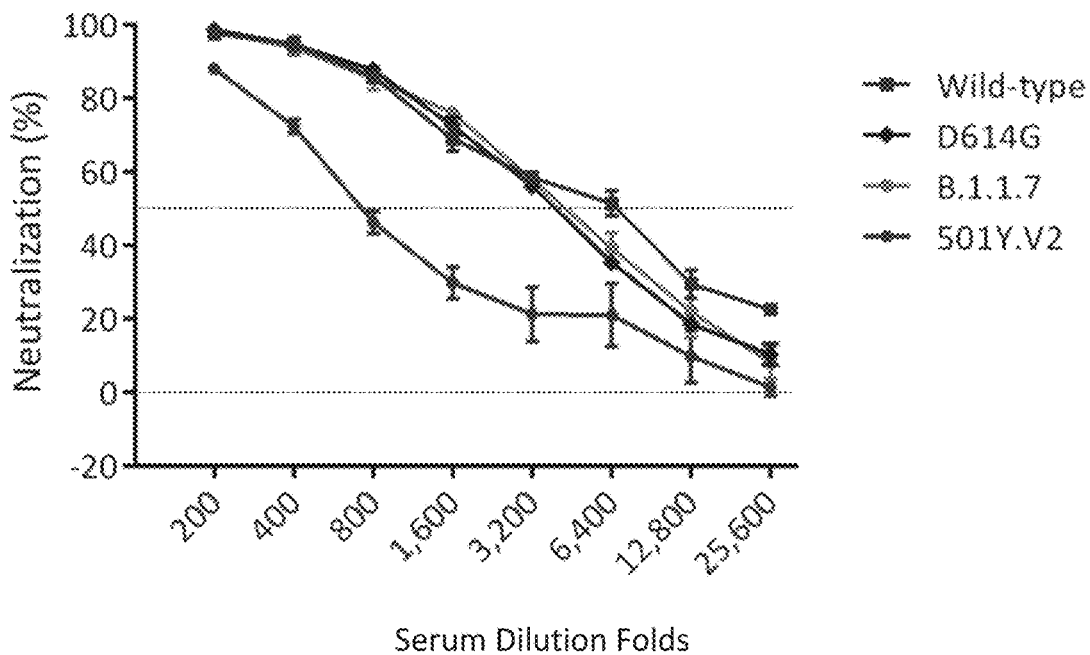
Figure 8:
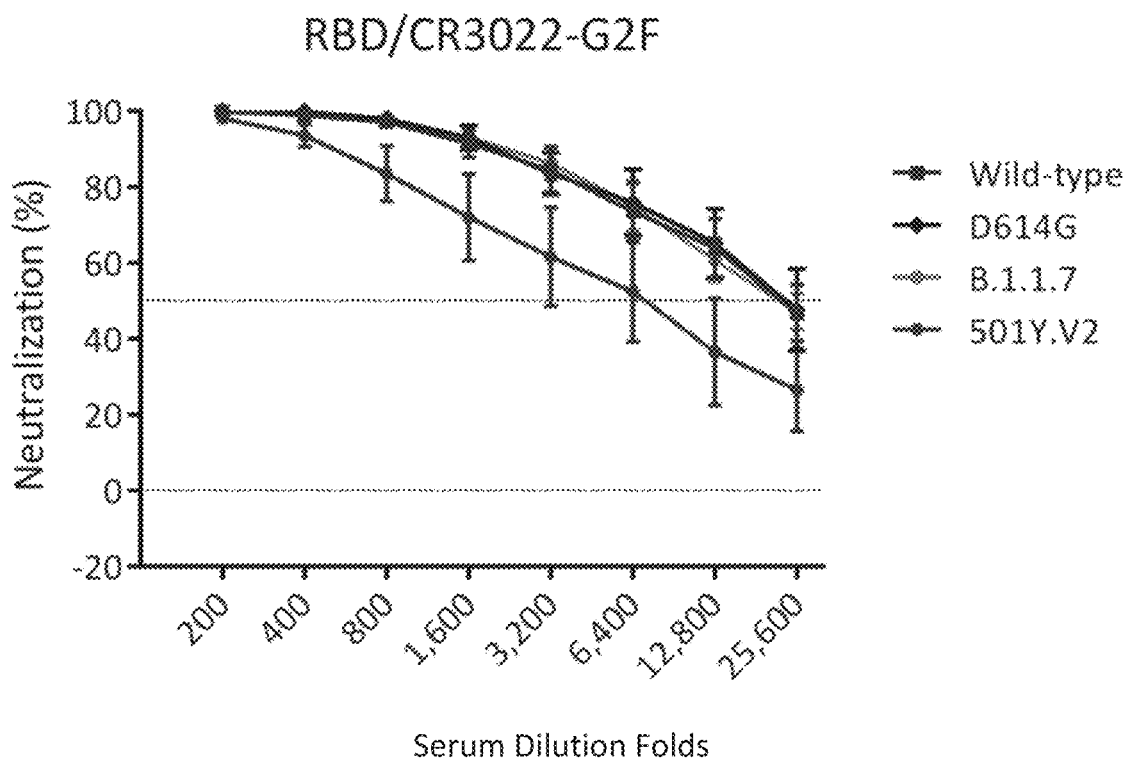
Figure 8:
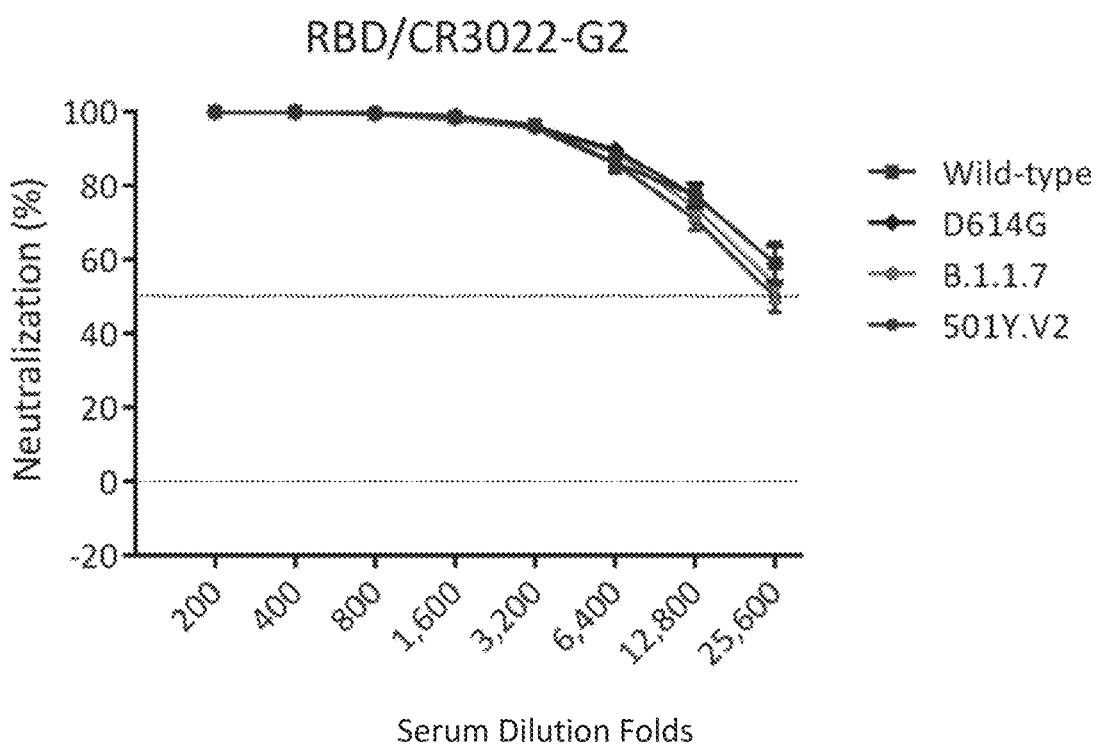
Figure 8:
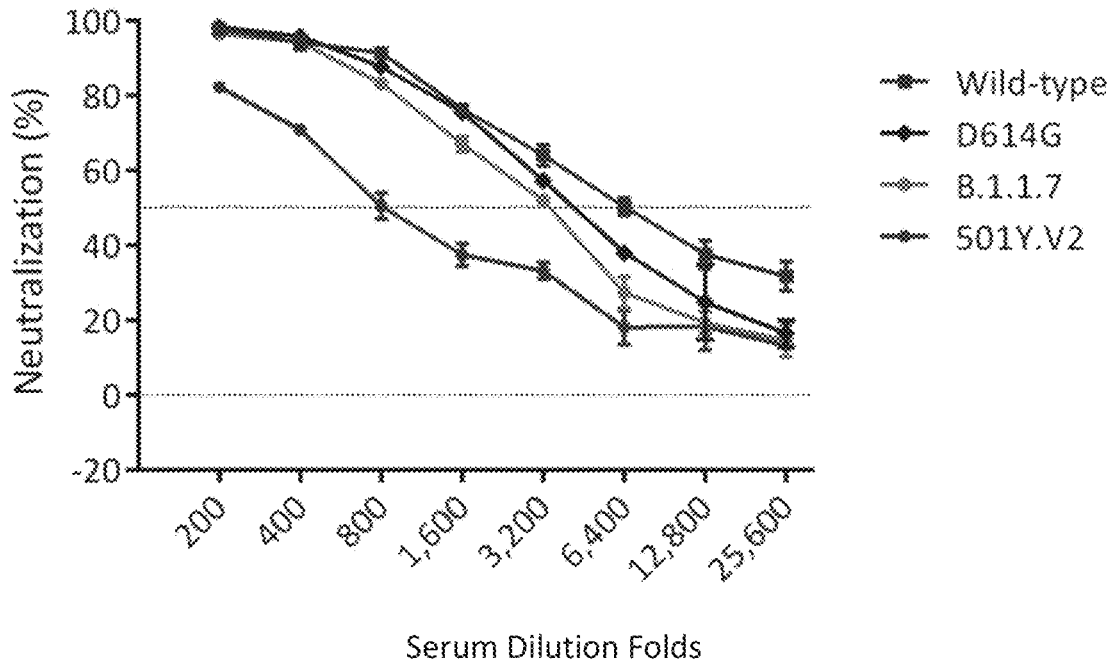
Figure 8:
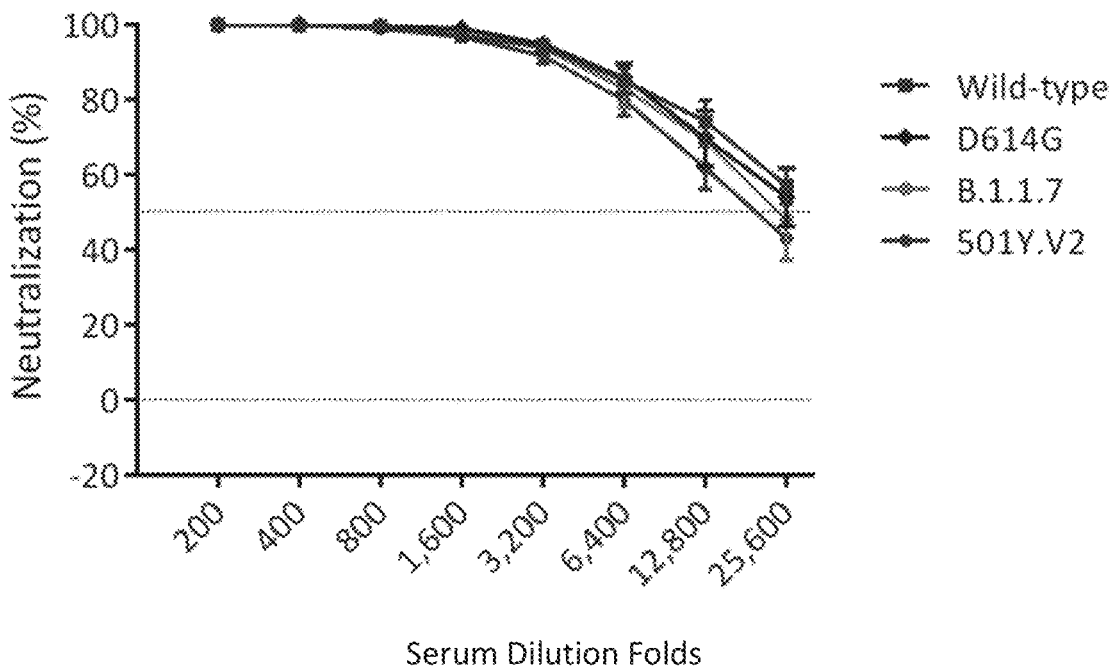
Figure 8:
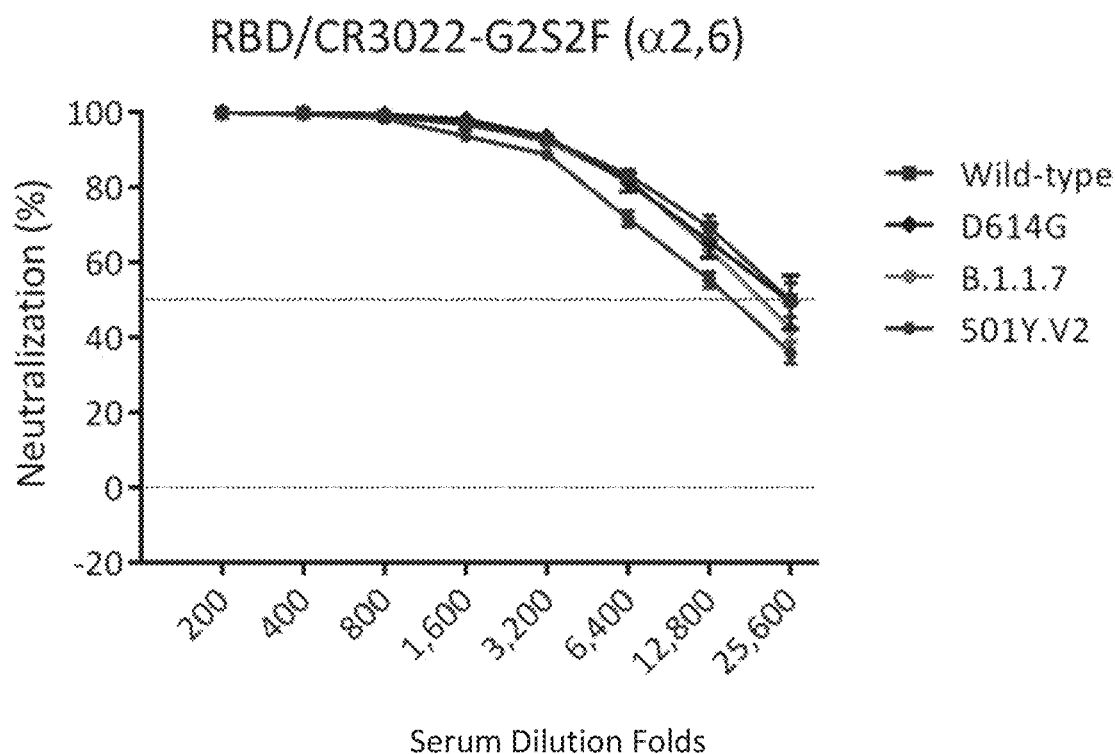
Figure 8:
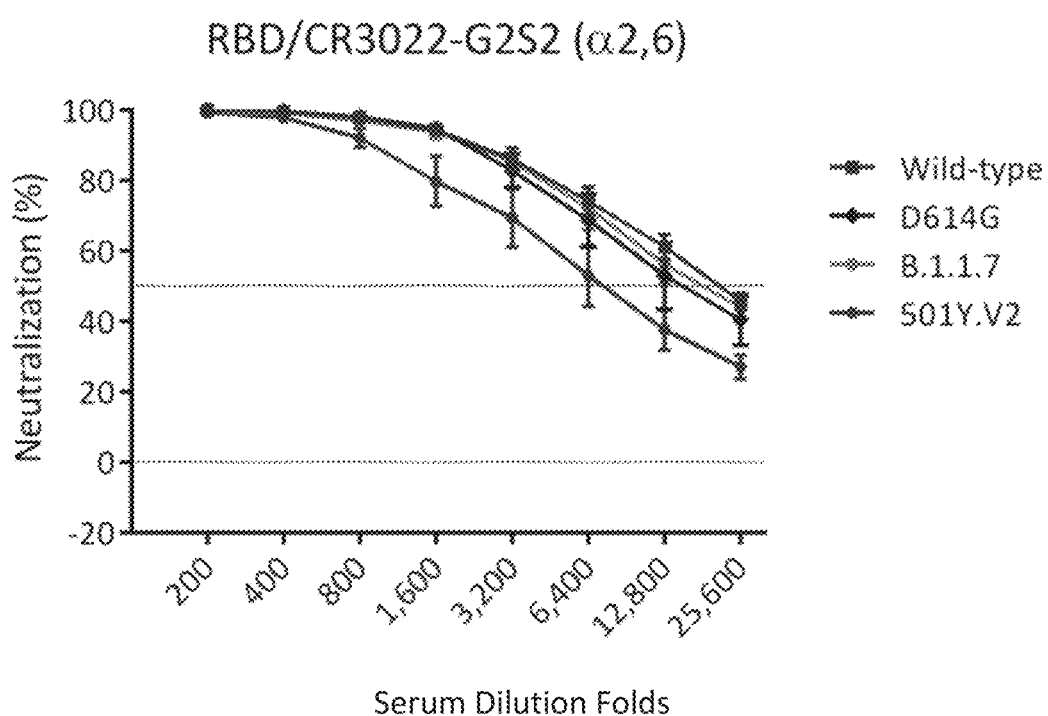

The results are shown in FIG. 8. A two-dose regimen of the immune complex vaccines comprising SARS-CoV-2 RBD and glycoengineered CR3022 variants, including G2F, G2, G2S2F (either alpha 2,3- or alpha 2,6-), and G2S2 (alpha 2,6-), can elicit robust broadly neutralizing antibodies against not only wild type virus, but also various SARS-CoV-2 mutant variants, including D614G, B.1.1.7, and the E484K-containing strain 501Y.v2. In contrast, the virus neutralization activity of antibodies elicited by RBD/original CR3022, RBD/CR3022-F241A (Alanine point mutation at residue F241) and RBD/CR3022-G2S1F (alpha 2,6) is significantly compromised, especially to the E484K-containing strain 501Y.v2.

Example 6 Results of Pseudovirus Neutralization Assay are Consistent with Those of SARS-CoV-2 (Strain hCoV19/Taiwan/4/2020)

Pathogen-free BALB/c mice (female, 6-week-old from BioLASCO) were used for vaccination study. SARS-CoV-2 RBD (10 μg) was delivered alone intramuscularly, or in complex with original or glycoengineered CR3022 at a molar ratio of 1:1 (Ag:Ab). All vaccines were adjuvanted with Adju-Phos (InvivoGen) and the final volume was brought to 100 μL with PBS, pH7.4 for each injection. Mice were primed and boosted via intramuscular injection at Day 1 and Day 21, respectively. Ten days after the boosting, mice were sacrificed and the blood was collected at Day 7 and Day 30 for ELISA and virus neutralization assays.

Figure 9:
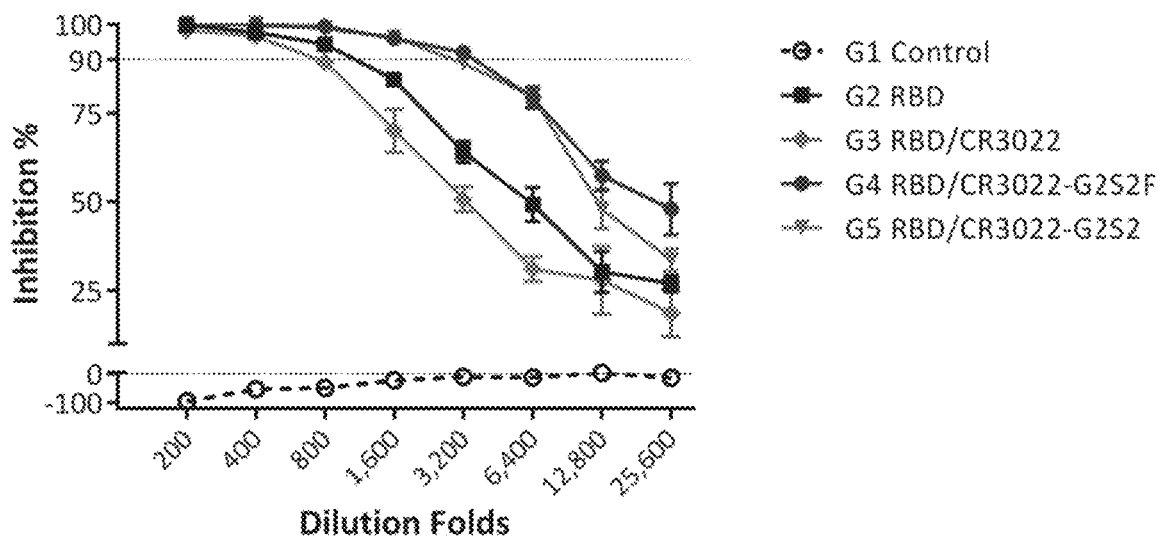
FIG. 9 shows the results of pseudovirus neutralization of Example 6.

G1: aluminum phosphate only, as control group
G2: 10 μg of SARS-CoV-2 RBD-His with aluminum phosphate
G3: immune complex (CR3022/SARS-CoV-2 RBD-His) with aluminum phosphate
G4: sialylated immune complex (CR3022-G2S2F/SARS-CoV-2 RBD-His) with aluminum phosphate
G5: sialylated immune complex (CR3022-G2S2/SARS-CoV-2 RBD-His) with aluminum phosphate SARS-CoV-2 spike pseudotyped lentivirus with luciferase reporter gene was used for determining the neutralization activities of serum RBD-specific IgGs induced by vaccines. As shown in the FIG. 9, RBD-specific antibodies induced by glycoengineered immune complex comprising SARS-CoV-2 RBD/CR3022-G2S2F (G4) and RBD/CR3022-G2S2 (G5) showed a higher neutralization activity. In contrast, RBD-specific antibodies induced by RBD (G2) or immune complex comprising SARS-CoV-2 RBD and CR3022 (G3) showed a significantly lower neutralization activity.

Figure 10:
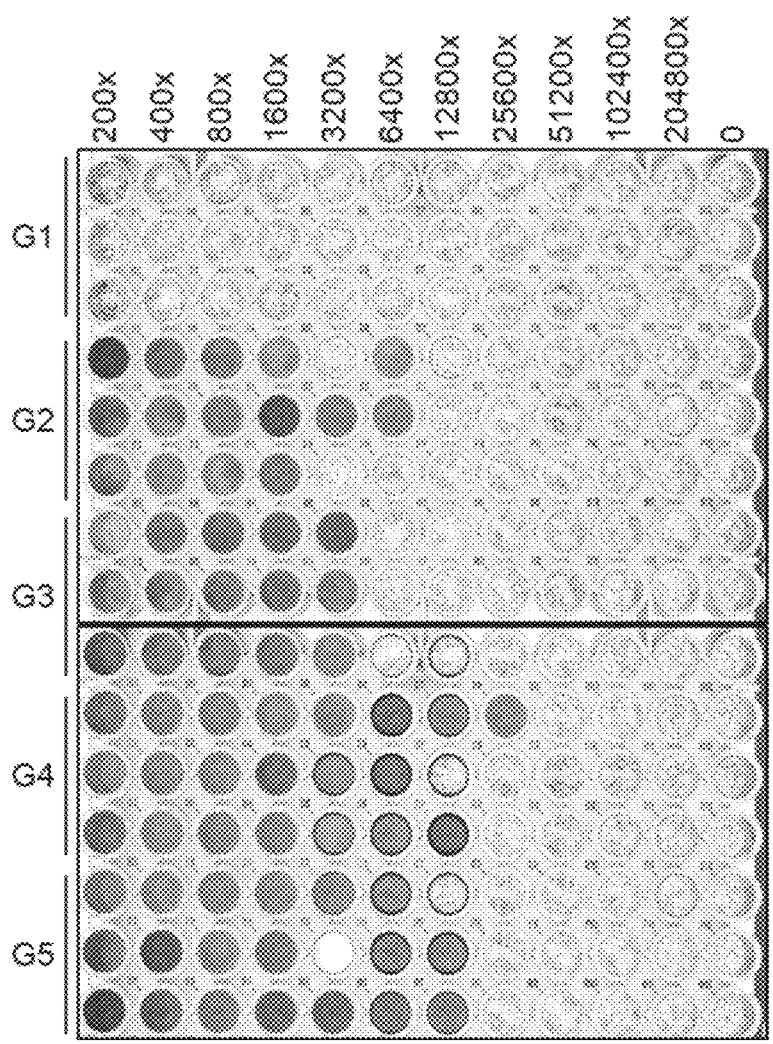
FIG. 10 shows the results of SARS-CoV-2 (strain hCoV19/Taiwan/4/2020) neutralization of Example 6.

SARS-CoV-2 (Strain hCoV19/Taiwan/4/2020) was used for determining the neutralization activities of serum RBD-specific IgGs induced by vaccines. Consistent with the results of pseudovirus neutralization assay, RBD-specific antibodies induced by glycoengineered immune complex comprising SARS-CoV-2 RBD/CR3022-G2S2F (G4) and RBD/CR3022-G2S2 (G5) showed a significantly higher neutralization activities, as comparing to other groups as shown in FIG. 10 and Table 6.

TABLE 6

| | | Protective Titer (Dilution folds) | |
| --- | --- | --- | --- |
| Group | Compositions | 50% | 90% |
| G1 | Control | <200 | <200 |
| G2 | RBD | 4,519 | 1,901 |
| G3 | RBD/CR3022 | 4,519 | 3,428 |
| G4 | RBD/CR3022-G2S2F | 18,071 | 8,433 |
| G5 | RBD/CR3022-G2S2 | 15,205 | 7,870 |

Example 7 Boosting Efficacy of Heterologous Prime-Boost of CHO-V10

A total of 15 female Balb/c at 6-8 weeks of age were purchased from BioLASCO Co., Ltd. Mice were randomly assigned to 3 groups after acclimation. The mice were received one or two doses of SARS-CoV-2 Spike (10 μg of Spike HexaProi)/Alhydrogel, and then boosted with one dose of CHO-V10 Candidate #1 (contains 10 μg of RBD) via IM route at a 3-week interval; or vaccinated with three doses of SARS-CoV-2 Spike (10 μg of Spike HexaPro)/Alhydrogel via IM route at a 3-week interval. The immune sera were collected at weeks 4 or 7 to assess the immunogenicity and pseudovirus neutralizing assays.

CHO-V10 Candidate #1: CR3022-G2S2F+RBD
IM: intramuscular
Virus Strain: SARS-CoV-2 wild-type (Wild-type), SARS-CoV-2 D614G mutant (D614G), SARS-CoV-2 alpha variant (Alpha), beta variant (Beta), gamma variant (Gamma) and delta variant (Delta) pseudoviruses.

Figure 11:
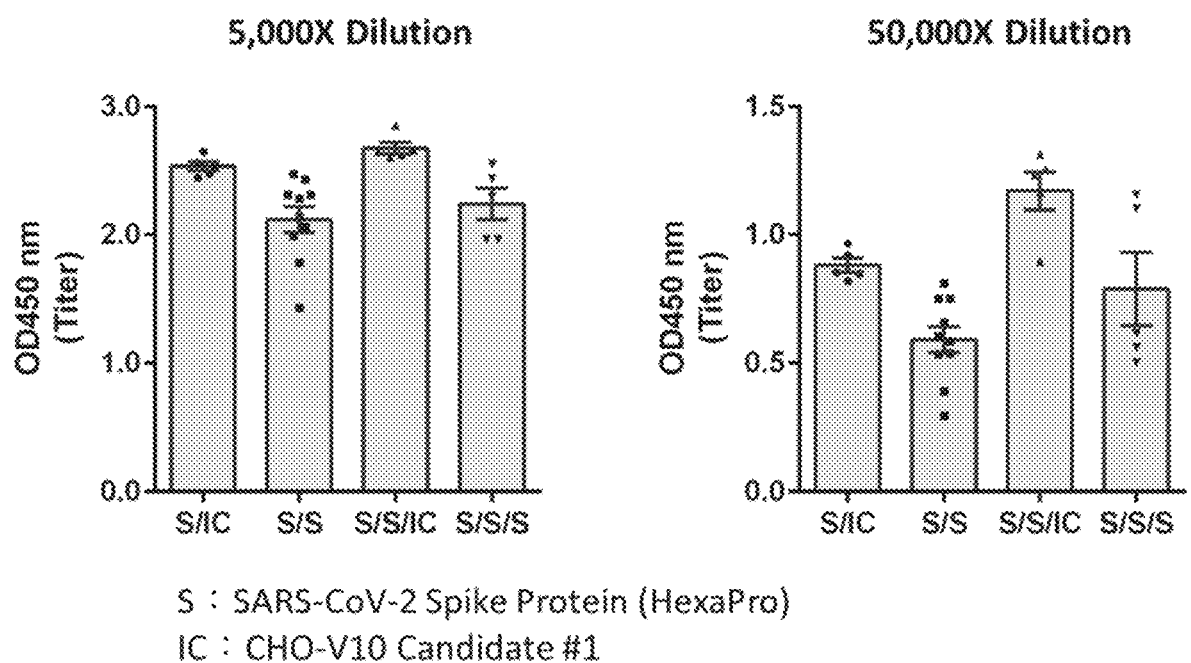
FIG. 11 shows the results of serum titer of anti-SARS-CoV-2 RBD IgG antibody of Example 7.

The immune sera were collected one week after the $2^{nd}$ and $3^{d}$ dosing, and the serum IgG titer against RBD was determined by ELISA as shown in FIG. 11. For mice received two doses of vaccine, heterologous prime-boost of Spike protein and CHO-V10 Candidate #1 induced a significantly higher titer than two doses of Spike protein. And for mice already vaccinated with two doses of Spike protein, boosting with one additional dose of CHO-V10 Candidate #1, but not Spike protein, significantly improved the serum IgG titer against RBD.

Figure 12:
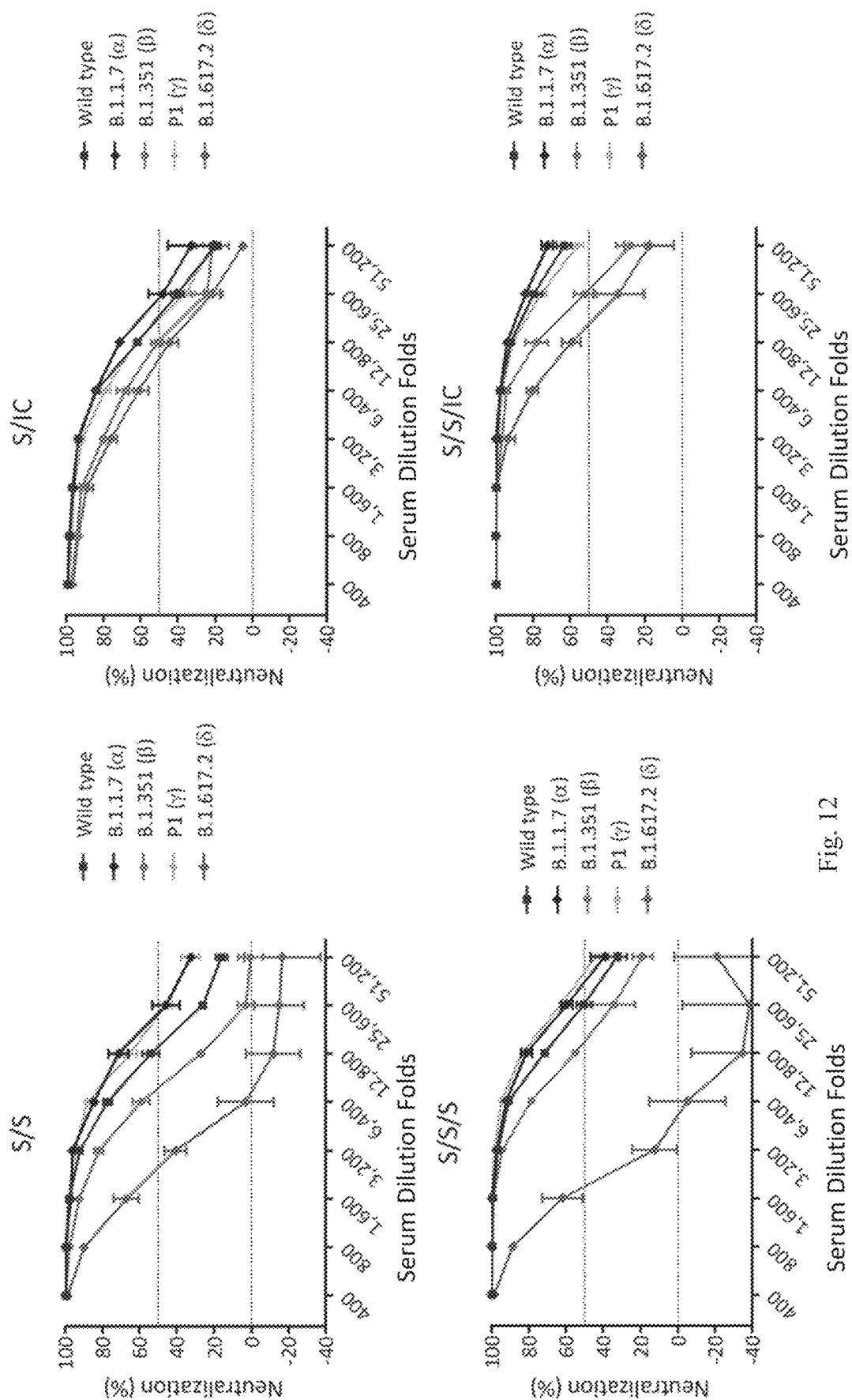
FIG. 12 shows pseudovirus neutralization assay of Example 7.

The results of pseudovirus neutralization assay are shown in FIG. 12. Vaccination with two doses of Spike protein can induce high titer (IC50>12,800×) of neutralizing antibodies to neutralize Wild-type, Alpha, and Gamma variants. But for Beta variant, the IC50 was reduced to 6,400×. And for Delta variant, the IC50 was significantly reduced to 1,600×-3,200×. Interestingly, boosting the mice which have immunized with one or two doses of Spike protein with one additional dose of CHO-V10 Candidate #1 can significantly increase the neutralizing antibody titer to VOCs, especially to Delta variant. In contrast, boosting S/S group with one additional dose of Spike protein did not improve the neutralizing activity to Delta variant.

Example 8 Pseudovirus Neutralization Assay on Gamma Variant, or Delta Variant

The main purpose of this Example is to investigate the vaccine efficacy RBD/CR3022-G2S2F (candidate #1) & RBD/CR3022-G2 (candidate #2).

Female Balb/c at 6-8 weeks of age were purchased from BioLASCO Co., Ltd. Mice were randomly assigned to 2 groups after acclimation. The mice were received two doses of RBD/CR3022-G2S2F (contains 10 µg of RBD) or RBD/CR3022-G2 (contains 10 µg of RBD) via IM route at a 3-week interval. The immune sera were collected at weeks 4 to assess the immunogenicity and pseudovirus neutralizing assays.

Virus Strain: SARS-CoV-2 wild-type (Wild-type), SARS-CoV-2 D614G mutant (D614G), SARS-CoV-2 alpha variant (Alpha), beta variant (Beta), gamma variant (Gamma) and delta variant (Delta) pseudoviruses.

Figure 13:
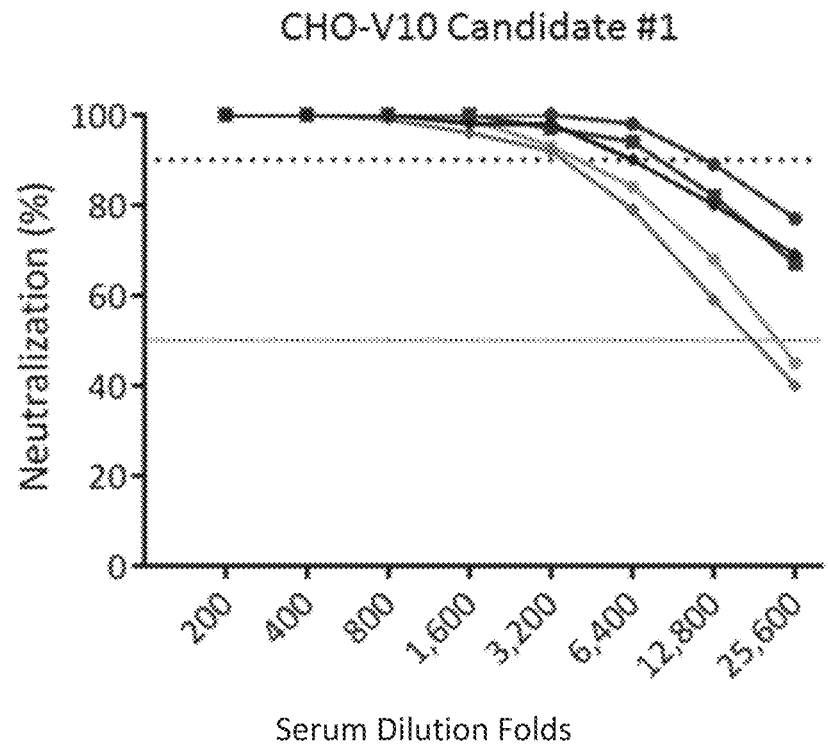
FIG. 13 shows the results of pseudovirus neutralization assay of Example 8.
Figure 13:
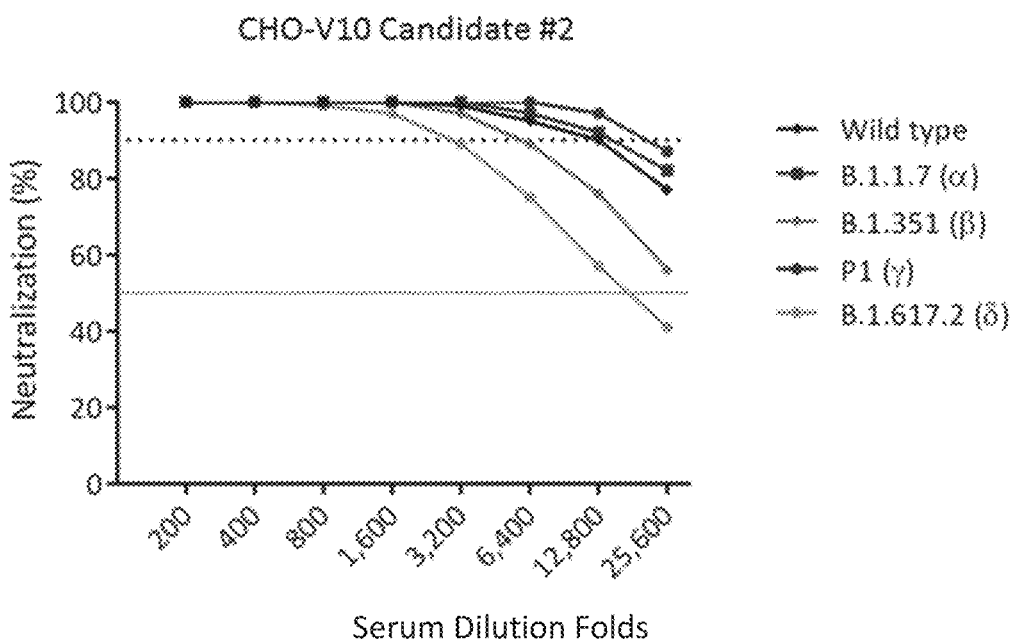

As shown in FIG. 13, the antibodies evoked by CHO-V10 Candidate #1 and Candidate #2 can effectively neutralize not only Wild-type, but also the VOCs currently announced by WHO with very high titers.

Example 9 SARS-CoV-2 Virus Challenging

The main purpose of this Example is to investigate the vaccine efficacy of CHO-V10 candidates in C57BL/6.

Female C57BL/6 and hACE2-Tg C57BL/6 at 6-8 weeks of age were purchased from BioLASCO Co., Ltd or The Jackson Laboratory, respectively. Mice were randomly assigned to groups (N=5-6 for each group) after acclimation. For C57BL/6 mice, mice were received 2 doses of Group 1 (G1)_RBD (10 µg)/aluminum phosphate, Group 2 (G2)_RBD (10 µg)/CR3022-G2S2F/aluminum phosphate, or Group 3 (G3)_RBD/CR3022-G2/aluminum phosphate at a 3-week interval. The immune sera were then collected for ELISA. To further study the protection ability of vaccine comprising RBD/CR3022-G2, SARS-CoV-2 virus challenging study was conducted in hACE2-Tg C57BL/6. First, mice were randomly assigned to two groups (n=6 for each group) and received 2 doses of PBS/aluminum phosphate or RBD (10 µg)/CR3022-G2/aluminum phosphate at a 3-week interval. Two weeks after the second does, the immunized hACE2-Tg C57BL/6 were challenged with SARS-CoV-2 virus (wild-type, $10^4$ TCID50). The body weight and temperature were monitored daily. Three mice were randomly selected and sacrificed for determining the virus RNA copy in lung at DPI (day post infection) 5 and DPI 10.

Figure 14:
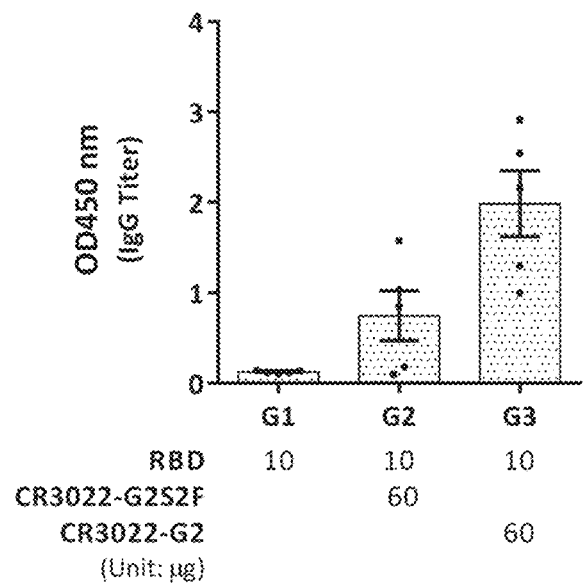
FIG. 14 shows the results of serum titer of anti-SARS-CoV-2 RBD IgG antibody in C57BL/6 mice of Example 9.

The results of serum titer of anti-SARS-CoV-2 RBD IgG antibody in C57BL/6 mice are shown in FIG. 14. The immune sera were collected one week after $1^{st}$ dose, and the serum IgG titer against RBD was determined by ELISA. As shown in FIG. 1, RBD/CR3022-G2 can induce the strongest anti-RBD IgG antibody in C57BL/6 mice after one dose immunization, as comparing to RBD/CR3022-G2S2F and RBD alone.

Figure 15:
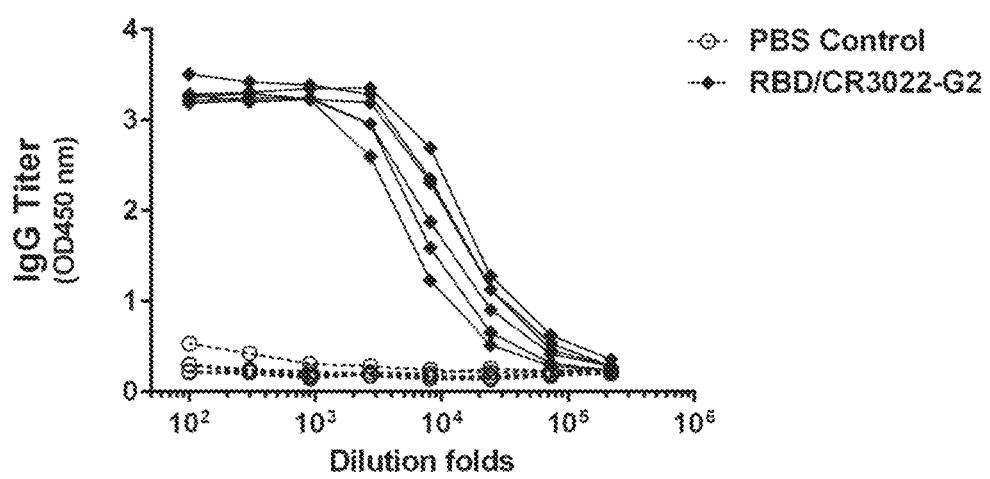
FIG. 15 shows the results of serum titer of anti-SARS-CoV-2 RBD IgG antibody in hACE2-Tg C57BL/6 mice of Example 9.

The results of serum titer of anti-SARS-CoV-2 RBD IgG antibody in hACE2-Tg C57BL/6 mice are shown in FIG. 15. The immune sera were collected one week after the $2^{nd}$ dose, and the serum IgG titer against RBD was determined by ELISA. As comparing to PBS control group, hACE2-Tg C57BL/6 mice received 2 doses of RBD/CR3022-G2 can elicit high titer of anti-RBD IgG antibody.

Figure 16A:
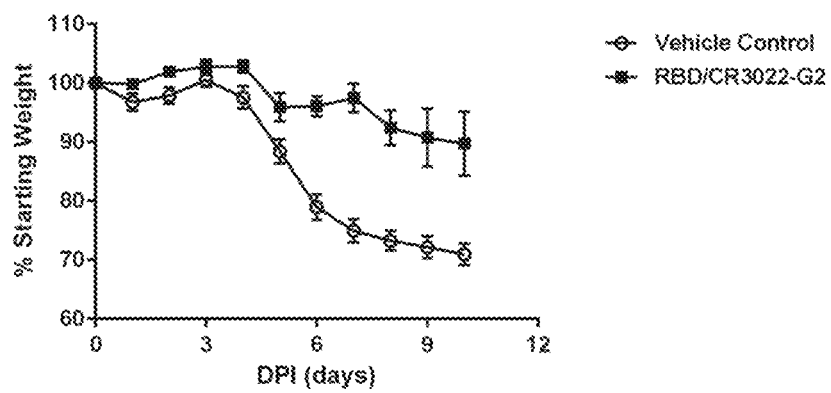
FIGS. 16A to 16C show the results of SARS-CoV-2 virus challenging of Example 9.
Figure 16B:
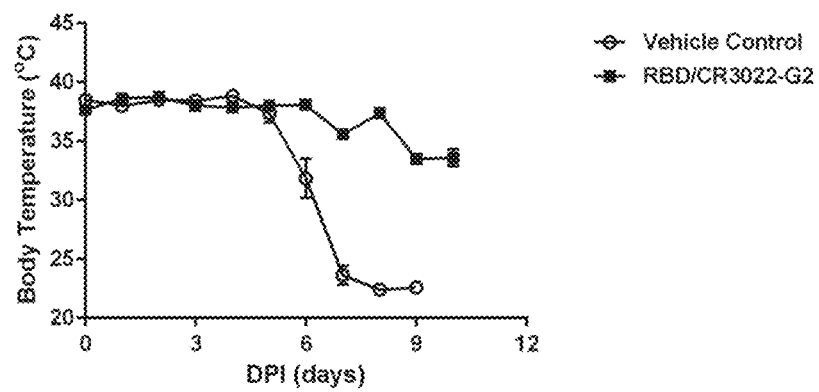
Figure 16C:
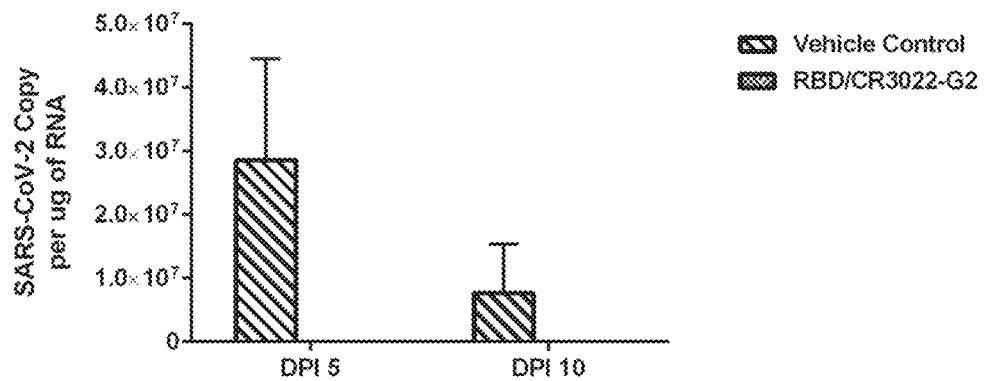

The results of SARS-CoV-2 virus challenging are shown in FIGS. 16A to 16C. Two weeks after the second dosing, the immunized mice were challenged with $10^4$ TCID50 of SARS-CoV-2 virus (wild-type). As shown in FIGS. 16A and 16B, the body weight and temperature of mice in control group started decreasing 5 days post virus infection, while the mice receiving 2 doses of RBD/CR3022-G2 remained unchanged. As shown in 16C, the virus RNA copies in lung tissues were determined at Day 5 and Day 10 post-infection. In control group mice, the average SARS-CoV-2 copy per g of lung RNA were $3 \times 10^7$ and $1 \times 10^7$ at DPI 5 and DPI 10, respectively. In vaccinated mice, the average SARS-CoV-2 copy per g of lung RNA were below the detection limit (<100) at both DPI 5 and DPI 10.

Example 10 Glycoengineered Immune Complexes Against HIV

The method of preparing glyco-engineering antibodies is as described in Example 1. The antibodies specific to gp120 of HIV are G0-PGT121, S-PGT121, or NS-PGT121 as described by Lofano et al., Sci. Immunol. 3, eaat7796 (2018). Biotinylated rgp120-YU2 (Immune Technology) was used as the antigen.

Pathogen-free BALB/c mice (female, 6-week-old from BioLASCO) were used for vaccination study. Biotinylated rgp120-YU2 (10 µg) was delivered alone intramuscularly, or in complex with original or glycoengineered G0-PGT121, S-PGT121, or NS-PGT121 at a ratio of 1:1 (Ag:Ab). The glycoengineered G0-PGT121, S-PGT121, or NS-PGT121 has a glycoengineered Fc that refers to an engineered N-glycan on the Fc region. The engineered N-glycan represented by the general formula (I) as below, and each of X and Y presents GlcNAc-, GalGlcNAc-, Sia(α2-3)GalGlcNAc-, or Sia(α2-6)GalGlcNAc-.

$$\begin{array}{c} X\text{-Man} \\ \diagdown \\ \phantom{X\text{-}}\text{Man-GlcNAc-GlcNAc-} \\ \diagup \phantom{\text{Man-GlcNAc-}} | \\ Y\text{-Man} \phantom{\text{Man-Glc}} (\text{Fuc})_{0\,or\,1} \end{array}$$

All vaccines were adjuvanted with Adju-Phos (InvivoGen) and the final volume was brought to 100 µL with PBS, pH7.4 for each injection. Mice were primed and boosted via intramuscular injection at Day 1 and Day 21, respectively. Ten days after the boosting, mice were sacrificed and the blood was collected for ELISA and virus neutralization assays. The results indicated that all vaccines prepared by immune complex comprising with glycoengineering antibody can induce a superior immune response when compared to immune complex comprising a non-glycoengineered antibody or antibody not defined in formula (I) such as X and Y are different.

Example 11 Glycoengineered Immune Complexes Against Influenza a Virus

The method of preparing glyco-engineering antibody is as described in Example 1. The antibodies specific to hemagglutinin (HA) of influenza A are F241A bispecific mAb as described by Maamary et al., PNAS, Sep. 19, 2017, vol. 114, no. 38, 10172-10177 and recombinant anti-HA mAb, PY102 as described by Dinca et al., Viral immunology. 1993; 6:75-84. Purified HA was used as the antigen.

Pathogen-free BALB/c mice (female, 6-week-old from BioLASCO) were used for vaccination study. HA (10 μg) was delivered alone intramuscularly, or in complex with original or glycoengineered F241A or PY102 at a ratio of 1:1 (Ag:Ab). The glycoengineered F241A or PY102 has a glycoengineered Fc that refers to an engineered N-glycan on the Fc region. The engineered N-glycan represented by the general formula (I) as below, and each of X and Y presents GlcNAc-, GalGlcNAc-, Sia(α2-3)GalGlcNAc-, or Sia(α2-6)GalGlcNAc-.

All vaccines were adjuvanted with Adju-Phos (InvivoGen) and the final volume was brought to 100 μL with PBS, pH7.4 for each injection. Mice were primed and boosted via intramuscular injection at Day 1 and Day 21, respectively. Ten days after the boosting, mice were sacrificed, and the blood was collected for ELISA and virus neutralization assays. The results indicated that all vaccines prepared by immune complex comprising with glycoengineering antibody can induce a superior immune response when compared to immune complex comprising a non-glycoengineered antibody or antibody not defined in formula (I) such as X and Y are different. Moreover, the antibodies induced by immune complex comprising with glycoengineering antibody showed the binding affinity not only to the used HA antigen, but also can binding to different types of HA.

While the present disclosure has been described in conjunction with the specific embodiments set forth, many alternatives thereto and modifications and variations thereof will be apparent to those of ordinary skill in the art. All such alternatives, modifications and variations are regarded as falling within the scope of the present disclosure.

What is claimed is:

1. A composition for inducing immune response comprising:
   a glycoengineered antibody or antigen-binding fragment thereof that is specific for an antigen portion having a receptor binding domain (RBD) of a surface protein of a virus, wherein the glycoengineered antibody or antigen-binding fragment thereof has a fragment crystallizable region (Fc region) and N-glycan on the Fc region, and the N-glycan is represented by the general formula (I)

$$\begin{array}{c} X\text{-Man} \\ \phantom{X\text{-M}}\diagdown \\ \phantom{XXXX}\text{Man-GlcNAc-GlcNAc-} \\ \phantom{X\text{-M}}\diagup \phantom{XXXXXXXX}| \\ Y\text{-Man} \phantom{XXXXXX} (\text{Fuc})_{0\text{ or }1} \end{array} \quad \text{formula (I)}$$

wherein:
each of X and Y presents GlcNAc-, GalGlcNAc-, Sia(α2-3)GalGlcNAc-, or Sia(α2-6) GalGlcNAc-, and X and Y are identical.

2. The composition of claim 1, further comprising the antigen portion having the RBD of the surface protein of the virus.

3. The composition of claim 1, wherein the surface protein is a spike protein.

4. The composition of claim 1, wherein the virus is coronavirus (CoV), human immunodeficiency virus, or Orthomyxoviridae.

5. The composition of claim 1, wherein the virus is alpha-CoV, beta-CoV, gamma-CoV, or delta-CoV.

6. The composition of claim 1, wherein the antigen portion comprises the amino acid sequence of SEQ ID NO: 1.

7. The composition of claim 1, wherein the N-glycan is selected from the group consisting of GlcNAc$_2$Man$_3$GlcNAc$_2$(Fuc) (G0F), GlcNAc$_2$Man$_3$GlcNAc$_2$ (G0), Gal$_2$GlcNAc$_2$Man$_3$GlcNAc$_2$(Fuc) (G2F), Gal$_2$GlcNAc$_2$Man$_3$GlcNAc$_2$ (G2), Sia$_2$(α2-3)Gal$_2$GlcNAc$_2$Man$_3$GlcNAc$_2$(Fuc) (G2S2F (alpha 2,3 linkage)), Sia$_2$(α2-6)Gal$_2$GlcNAc$_2$Man$_3$GlcNAc$_2$(Fuc) (G2S2F (alpha 2,6 linkage)), Sia$_2$(α2-6)Gal$_2$GlcNAc$_2$Man$_3$GlcNAc$_2$ (G2S2 (alpha 2,6 linkage)), and Sia$_2$(α2-3)Gal$_2$GlcNAc$_2$Man$_3$GlcNAc$_2$ (G2S2 (alpha 2,3 linkage)).

8. The composition of claim 1, wherein a plurality of the glycoengineered antibodies or antigen-binding fragment thereof are provided in a population, and more than about 90% of the population has the same N-glycan.

9. A composition for inducing immune response comprising:
   a glycoengineered antibody or antigen-binding fragment thereof that is specific for an antigen portion having a receptor binding domain (RBD) of a surface protein of a virus, wherein the glycoengineered antibody or antigen-binding fragment thereof has a fragment crystallizable region (Fc region) and N-glycan on the Fc region, and the N-glycan is represented by the general formula (I)

$$\begin{array}{c} X\text{—Man} \\ \phantom{X\text{—M}}\diagdown \\ \phantom{XXXX}\text{Man—GlcNAc—GlcNAc—} \\ \phantom{X\text{—M}}\diagup \phantom{XXXXXXXXX}| \\ Y\text{—Man} \phantom{XXXXXXX} (\text{Fuc})_{0\text{ or }1} \end{array} \quad \text{formula (I)}$$

wherein:
each of X and Y presents a glycan, and X and Y are identical, wherein the glycoengineered antibody or antigen-binding fragment thereof comprises a heavy chain variable region comprising the amino acid sequence of SEQ ID NO: 2 or a substantially similar sequence thereof; and a light chain variable region comprising the amino acid sequence of SEQ ID NO: 3 or a substantially similar sequence thereof.

10. An immune combination comprising an effective amount of the composition of claim 1 and an effective amount of the antigen portion having the RBD of the surface protein of the virus and a pharmaceutically acceptable carrier and/or adjuvant.

11. The immune combination of claim 10, wherein the immune combination further comprises a vaccine of the virus.

12. The immune combination of claim 11, wherein the vaccine comprises the antigen portion.

13. A method for treating an infection by a coronavirus in a subject in need of such treatment comprising administering an effective amount of the composition of claim 1 to the subject.

14. The method of claim 13, wherein the coronavirus is alpha-CoV, beta-CoV, gamma-CoV, or delta-CoV2.

15. The method of claim 13, wherein the method is for neutralizing the coronavirus and/or enhancing antibody-dependent cell-mediated cytotoxicity (ADCC) in the subject.

16. A method for treating an infection by a coronavirus in a subject in need of such treatment comprising administering an effective amount of the composition of claim 2 to the subject.

17. The method of claim 16, wherein the coronavirus is alpha-CoV, beta-CoV, gamma-CoV, or delta-CoV2.

18. The method of claim 16, wherein the method is for neutralizing the coronavirus and/or enhancing ADCC in the subject.

19. A method for treating an infection by a coronavirus in a subject in need of such treatment comprising administering an effective amount of the immune combination of claim 10 to the subject, where the RBD is from a coronavirus.

20. The method of claim 19, wherein the composition and the coronavirus RBD are co-administered simultaneously, separately or sequentially or co-administered in combination as a coformulation.

21. The method of claim 19, wherein the immune combination further comprises a vaccine of the coronavirus.

22. The method of claim 21, wherein the vaccine is administered prior to the composition.

23. The method of claim 19, wherein the method comprises administering the composition at least two times.

24. The method of claim 19, wherein the coronavirus is alpha-CoV, beta-CoV, gamma-CoV, or delta-CoV2.

25. The method of claim 19, wherein the method is for priming and subsequently boosting an immune response at different times.

26. The method of claim 19, wherein the method is for neutralizing the coronavirus and/or enhancing ADCC in the subject.

27. A composition for inducing immune response comprising:
   a glycoengineered antibody or antigen-binding fragment thereof comprising means for binding a receptor binding domain (RBD) of a surface protein of a virus, wherein the glycoengineered antibody or antigen-binding fragment thereof further comprises a fragment crystallizable region (Fc region) and N-glycan on the Fc region, and the N-glycan is represented by the general formula (I)
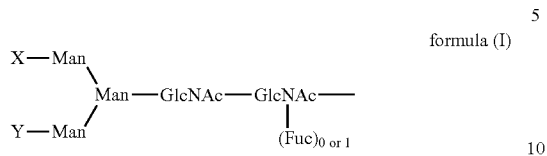
formula (I)
wherein:
each of X and Y presents GlcNAc-, GalGlcNAc—, Sia(α2-3)GalGlcNAc-, or Sia(α2-6)GalGlcNAc-, and X and Y are identical.
* * * * *

SEQUENCE LISTING

```
<160> NUMBER OF SEQ ID NOS: 3

<210> SEQ ID NO 1
<211> LENGTH: 223
<212> TYPE: PRT
<213> ORGANISM: SARS-CoV-2

<400> SEQUENCE: 1
```

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

```
Pro Lys Lys Ser Thr Asn Leu Val Lys Asn Lys Cys Val Asn Phe
    210                 215                 220
```

<210> SEQ ID NO 2
<211> LENGTH: 117
<212> TYPE: PRT
<213> ORGANISM: Homo sapiens

<400> SEQUENCE: 2

```
Gln Met Gln Leu Val Gln Ser Gly Thr Glu Val Lys Lys Pro Gly Glu
1               5                   10                  15

Ser Leu Lys Ile Ser Cys Lys Gly Ser Gly Tyr Gly Phe Ile Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Gly Gly Ser Gly Ile Ser Thr Pro Met Asp Val Trp Gly Gln Gly
            100                 105                 110

Thr Thr Val Thr Val
        115
```

<210> SEQ ID NO 3
<211> LENGTH: 113
<212> TYPE: PRT
<213> ORGANISM: Homo sapiens

<400> SEQUENCE: 3

```
Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys
```